(12) United States Patent
Choi et al.

(10) Patent No.: US 12,263,481 B2
(45) Date of Patent: Apr. 1, 2025

(54) MICROCHIP FOR ANALYZING FLUIDS

(71) Applicant: SMALL MACHINES, Daejeon (KR)

(72) Inventors: Jun Kyu Choi, Seoul (KR); Gyeong Woo Kang, Seoul (KR); Na Hyun Song, Namyangju-si (KR)

(73) Assignee: SMALL MACHINES, Seoul (KR)

( * ) Notice: Subject to any disclaimer, the term of this patent is extended or adjusted under 35 U.S.C. 154(b) by 302 days.

(21) Appl. No.: 16/618,266

(22) PCT Filed: Jul. 17, 2017

(86) PCT No.: PCT/KR2017/007650
§ 371 (c)(1),
(2) Date: Nov. 29, 2019

(87) PCT Pub. No.: WO2018/221784
PCT Pub. Date: Dec. 6, 2018

(65) Prior Publication Data
US 2020/0147611 A1    May 14, 2020

(30) Foreign Application Priority Data

Jun. 1, 2017    (KR) .......................... 10-2017-0068512

(51) Int. Cl.
*B01L 3/00*    (2006.01)
*G01N 33/543*    (2006.01)
(Continued)

(52) U.S. Cl.
CPC .. *B01L 3/502761* (2013.01); *G01N 33/54326* (2013.01); *G01N 33/582* (2013.01);
(Continued)

(58) Field of Classification Search
CPC ....... B01L 3/502761; B01L 2200/0647; B01L 2200/10; B01L 2300/0681;
(Continued)

(56) References Cited

U.S. PATENT DOCUMENTS

2009/0321662 A1* 12/2009 Ohtsuka ................. G01N 21/05
250/576
2011/0243795 A1* 10/2011 Park .................. B01L 3/502746
422/68.1
(Continued)

FOREIGN PATENT DOCUMENTS

CN    103575882 B  * 11/2015   ........... G01N 33/537
EP    1495799 A2  *  1/2005   ........ B01L 3/502746
(Continued)

OTHER PUBLICATIONS

Zeng et al (Ultrasensitive microfluidic solid-phase ELISA using an actuatable microwell-patterned PDMS chip, Lab on a Chip, 2013, vol. 13, pp. 4190-4197 (Year: 2013).*
(Continued)

*Primary Examiner* — Paul S Hyun
*Assistant Examiner* — Jean C. Caraballo-Leon
(74) *Attorney, Agent, or Firm* — Sughrue Mion, PLLC

(57) ABSTRACT

A microchip includes a body having an upper surface and a lower surface and a plurality of inner channels formed between the upper surface and the lower surface in which the plurality of inner channels include an input channel configured to receive an assay sample including target antigens and injected through a though hole, a reaction channel configured to be in fluid communication with the input channel and including magnetic particle-first antibody complexes to be subjected to a first antigen-antibody reaction with the target antigens, the magnetic particle-first antibody complexes including magnetic particles and first antibodies, and a detection channel configured to be in fluid communication with the reaction channel and including second antibodies to be subjected to a second antigen-antibody reaction with the immune complexes flowed from the reaction channel.

16 Claims, 20 Drawing Sheets

(51) Int. Cl.
    *G01N 33/58*     (2006.01)
    *G01N 35/00*     (2006.01)

(52) U.S. Cl.
    CPC .. *G01N 35/0098* (2013.01); *B01L 2200/0647* (2013.01); *B01L 2200/10* (2013.01); *B01L 2300/0681* (2013.01); *B01L 2400/086* (2013.01)

(58) Field of Classification Search
    CPC ......... B01L 2400/086; B01L 3/502753; B01L 2400/043; B01L 2200/0668; G01N 33/54326; G01N 33/582; G01N 35/0098; G01N 33/54333; G01N 2015/1006; G01N 15/1484; G01N 2015/1486; G01N 15/1463; G01N 15/14
    See application file for complete search history.

(56) References Cited

U.S. PATENT DOCUMENTS

| | | | |
|---|---|---|---|
| 2012/0031773 A1* | 2/2012 | Miller | G01N 33/5438 205/777.5 |
| 2012/0276641 A1* | 11/2012 | Dimov | B01L 3/50273 436/63 |
| 2013/0224848 A1* | 8/2013 | Gandini | G01N 33/54326 435/287.2 |
| 2014/0120633 A1* | 5/2014 | Gandini | B01L 3/5027 436/501 |
| 2015/0198593 A1* | 7/2015 | Barry | G01N 27/447 436/501 |
| 2015/0231627 A1* | 8/2015 | Sloan | A61B 5/150343 422/534 |
| 2016/0123978 A1* | 5/2016 | De Le O E Flores | B01L 3/502715 506/9 |
| 2016/0169883 A1* | 6/2016 | Tsukamto | G01N 27/403 435/7.92 |

FOREIGN PATENT DOCUMENTS

| | | | |
|---|---|---|---|
| KR | 10-0961874 B1 | 6/2010 | |
| KR | 10-2011-0024846 A | 3/2011 | |
| KR | 10-2012-0056442 A | 6/2012 | |
| KR | 20120056442 A * | 6/2012 | |
| KR | 10-2013-0063775 A | 6/2013 | |
| KR | 10-2015-0050110 A | 5/2015 | |
| KR | 10-2017-0045983 A | 4/2017 | |
| WO | WO-2013010178 A1 * | 1/2013 | ............... C12Q 1/00 |
| WO | 2014/007248 A1 | 1/2014 | |

OTHER PUBLICATIONS

Welch et al (Orientation and characterization of immobilized antibodies for improved immunoassays (Review), Biointerphases, 2017, vol. 12, pp. 02D301-1 to 02D301-13 (Year: 2017).*
Bieke Van Dorst et al., "Integration of an optical CMOS sensor with a microfluidic channel allows a sensitive readout for biological assays in point-of-care tests", Biosensors and Bioelectronics, 2016, pp. 126-131, vol. 78.
Korean Notice of Allowance for 10-2017-0068512 dated May 13, 2019.
International Search Report for PCT/KR2017/007650 dated, Mar. 14, 2018.

* cited by examiner

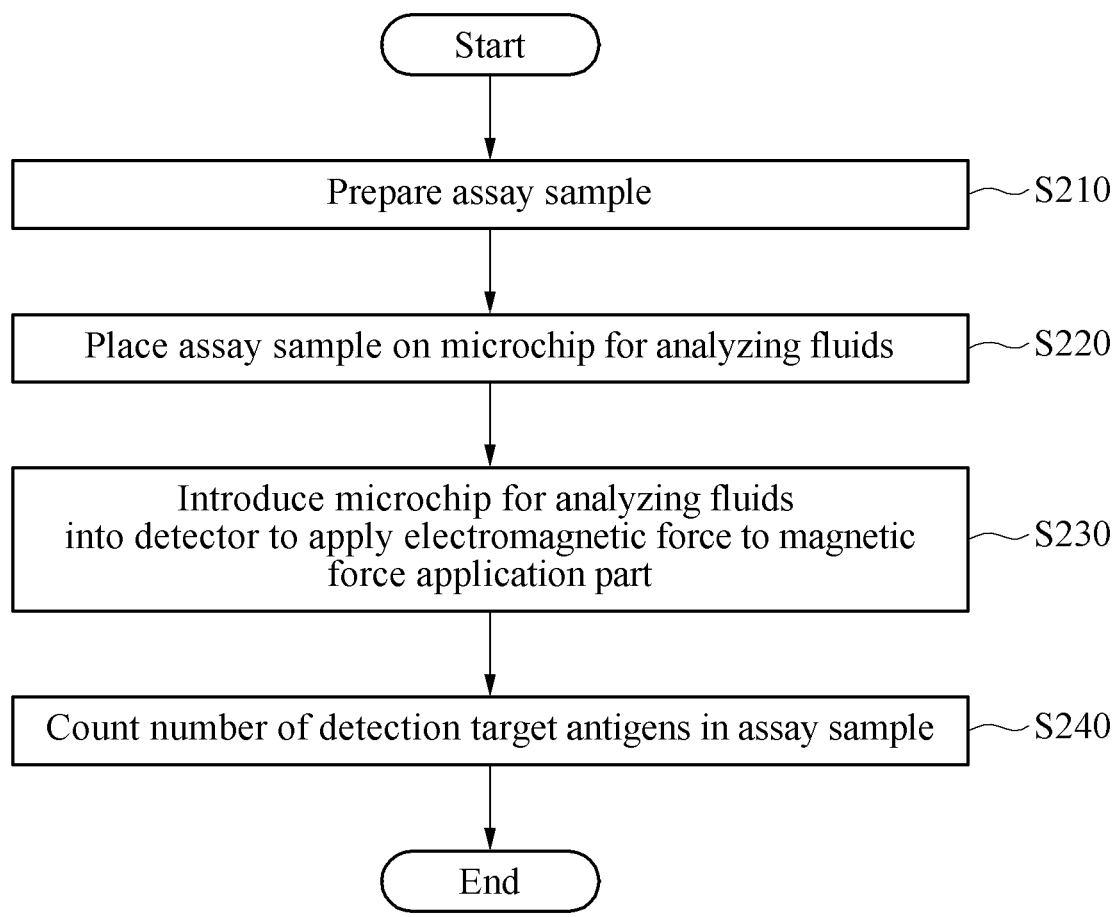

FIG. 3F
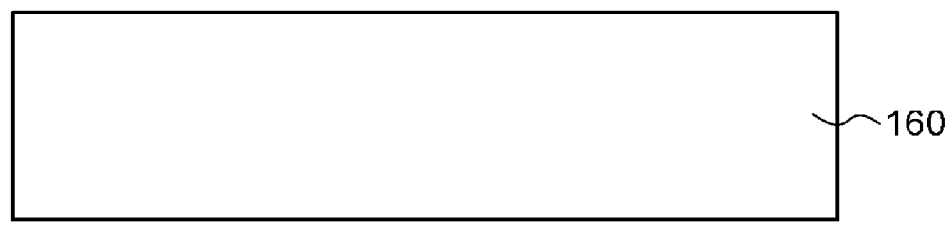
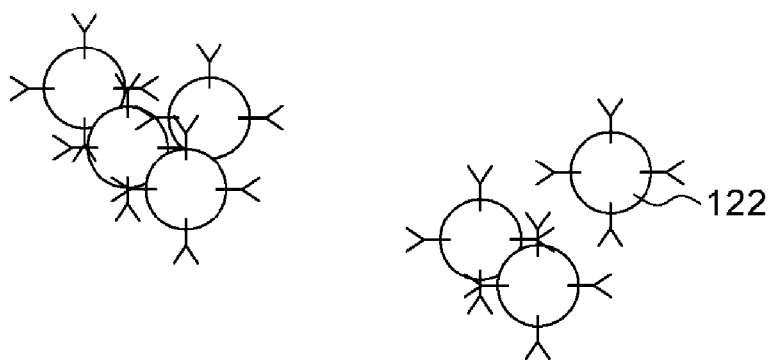
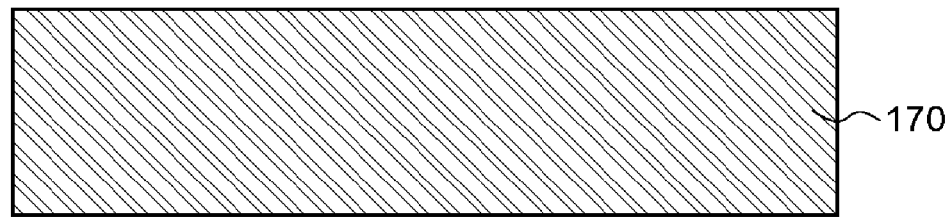

MICROCHIP FOR ANALYZING FLUIDS

CROSS-REFERENCE TO RELATED APPLICATIONS

This application is a National Stage of International Application No. PCT/KR2017/007650 filed on Jul. 17, 2017, claiming the priority benefit of Korean Patent Application No. 10-2017-0068512, filed on Jun. 1, 2017 in the Korean Intellectual Property Office, the disclosure of which is incorporated herein by reference.

TECHNICAL FIELD

The present invention relates to a microchip for analyzing fluids, and more particularly to a microchip for analyzing fluids including a plurality of channels functionally configured to easily detect a detection target substance present in a fluid, and a method of detecting a detection target substance using the microchip.

BACKGROUND ART

Various chip structures have been developed and used to provide miniaturized analytical methods and diagnostic equipment that allows more efficient analysis of fluid samples. Lab-on-a-chip technology enables various functions to be performed on one chip to increase analysis and disease diagnosis efficiency and quickly manufacture a diagnostic kit.

The lab-on-a-chip technology enables implementation of a variety of experiments, such as sample separation, purification, mixing, labeling, analysis, and cleaning, to be performed in the laboratory on small size chips. In designing a lab-on-a-chip, microfluidics, microfluidic control system-related technology, and microelectromechanical system (MEMS) technology are used.

In the case of microchips (or structures) with microchannels that embody microfluidics, a method of causing a fluid to move by the capillary phenomena by using small motors or by limiting the width and height of the microchannels such that the fluid moves into a space formed by the microchannels inside the chip may be used.

In microchips, the capillary force of which is the main driving force that causes fluid movement, the action force due to interaction between the upper and lower inner walls of microchannels and a fluid, and the action force due to interaction between left and right inner walls of the microchannels and the fluid may be different. As a result, a fluid flowing through spaces formed by the microchannels may have irregular and nonuniform movement patterns. Furthermore, such non-uniform flow patterns may become a major obstacle to the detection and analysis of a detection target substance present in a trace amount in a fluid sample.

Accordingly, there is a need for development of a novel microchip for analyzing fluids, to which a new technology for inducing fluid movement is applied and which is capable of providing a uniform fluid movement pattern and providing improved sensitivity to detection of a detection target substance.

The background art of the invention has been described to facilitate understanding of the present invention. It should not be understood that the matters described in the background form as prior art of the present invention.

DISCLOSURE

Technical Problem

To address problems of microchips for analyzing fluids embodied by capillary force, the prior art has proposed a method of forcibly flowing fluid through pumping action of an external pump to secure a required flow rate. However, such an approach may create bubbles in a fluid sample, thereby causing errors in analysis. Further, the configuration of a chip may be complicated, thereby increasing manufacturing time and costs and complicating an inspection process.

Meanwhile, a fluorescent substance-labeled antibody previously immobilized on a microchip may be used to analyze a trace amount of target substance contained in a fluid sample such as blood or body fluid. In particular, a detection target substance present in a fluid sample may be indirectly identified by measuring the intensity of light detected by irradiating a microchip for analyzing fluids, into which a fluid sample is injected, with light. However, upon detection using a fluorescent substance-based microchip for analyzing fluids, detection errors may occur due to fluorescent substances that are not bound to detection target substances in channels, or fluorescent substance-detection target substance complexes that are bound to substances to be analyzed, but are not immobilized and float in the chip. To address such a problem, a fluorescent substance-based microchip for analyzing fluids necessarily requires a washing process, whereby an inspection process may also be complicated.

Accordingly, the present inventors have recognized that the above problems can be solved by using magnetic particles with no fluorescent substance or optical label and, as a result, have invented a microchip for analyzing fluids which has no optical label, fluid therein flows by capillary force, and is capable of more accurately detecting a target substance.

Further, the present inventors have recognized that a trace amount of detection target substance can be detected from a trace amount of fluid sample by increasing the efficiency of an immune response between magnetic particles, to which an antibody is attached, and detection target substances using magnetic properties. In addition, the present inventors found that self-assembly due to a non-specific immune response did not occur, and determined an optically countable size of magnetic particle.

Accordingly, it is an object of the present invention to provide a microchip for analyzing fluids which can increase the efficiency of an immune response with a detection target substance and allow quantitative optical analysis of the detection target substance even without use of a fluorescent substance.

Further, it is another object of the present invention to provide a method of quantitating an antigen using the microchip for analyzing fluids according to the present invention.

It will be understood that technical problems of the present invention are not limited to the aforementioned problems and other technical problems not referred to herein will be clearly understood by those skilled in the art from disclosures below.

Technical Solution

In accordance with an aspect of the present invention, the above and other objects can be accomplished by the provision of a microchip for analyzing fluids, the microchip including a body that includes an upper surface and a lower surface, wherein fluid flows to internal channels formed between the upper surface and the lower surface to detect a specific antigen in the fluid, wherein the internal channels include an input channel configured such that an assay sample is injected through a through hole penetrating the upper surface; a reaction channel configured to be in fluid communication with the input channel, to include magnetic particles on which a first antibody is immobilized, to include magnetic particles to which the first antibody, subjected to a first antigen-antibody reaction with the assay sample having flowed from the input channel, is immobilized, wherein the magnetic particles form immune complexes through the first antigen-antibody reaction, and to have a higher height than the lower surface forming the input channel; and a detection channel configured to be in fluid communication with the reaction channel, to include a second antibody, subjected to a second antigen-antibody reaction with the immune complexes having flowed from the reaction channel, immobilized thereon, and to have a longer length and narrower width than the input channel or the reaction channel.

According to an aspect of the present invention, a height of the lower surface of the reaction channel may be lowered from a start portion of the reaction channel toward the detection channel.

According to another aspect of the present invention, the magnetic particles may have a particle diameter of 0.1 to 6.0 µm.

According to another aspect of the present invention, the first antibody and the second antibody may be different from a fluorescence-labeled antibody.

According to another aspect of the present invention, the magnetic particles may be attached to the upper surface that forms the reaction channel.

According to another aspect of the present invention, the first antibody may be a monoclonal antibody, and the second antibody may be a polyclonal antibody.

According to another aspect of the present invention, the input channel may include a filter.

According to another aspect of the present invention, the detection channel may include a plurality of wells, and the second antibody may be immobilized in the wells via a linker molecule.

According to another aspect of the present invention, a diameter and depth of the wells may be 1.2 to 2.0 times a particle diameter of the magnetic particles.

According to another aspect of the present invention, the detection channel may further include a plurality of capture pillars, and the second antibody may be immobilized between the capture pillars.

Each of the plurality of pillars may be arranged to have an interval of 1.2 to 2.0 times the particle diameter of the magnetic particles.

According to another aspect of the present invention, when the microchip for analyzing fluids is introduced into a detector including a magnetic material capable of attracting or repelling the magnetic particles, the second antibody may have a position corresponding to the magnetic material.

According to another aspect of the present invention, an intensity of a magnetic field of a magnetic material corresponding to a surface to which the second antibody is attached may be greater than an intensity of a magnetic field of a magnetic material corresponding to a surface to which the second antibody is not attached.

According to another aspect of the present invention, the microchip for analyzing fluids may further include flow control pillars for controlling flow of the assay sample, wherein the flow control pillars may be attached to the upper surface that forms the input channel, the reaction channel, or the detection channel.

According to another aspect of the present invention, the first antibody may be attached in a number of $10^5$ times the square of a radius of the magnetic particles.

In accordance with another aspect of the present invention, there is a method of quantitating an antigen, the method including: preparing an assay sample; positioning the assay sample on the microchip for analyzing fluids; introducing the microchip for analyzing fluids into a detector including a magnetic force application part and a CMOS image sensor and applying electromagnetic force to the magnetic force application part; and counting the number of a detection target antigen in the assay sample using the CMOS image sensor.

According to an aspect of the present invention, the magnetic force application part may include a first magnetic force application part constituted of a plurality of magnetic material pairs in the detector, and the applying of electromagnetic force to the magnetic force application part may include applying electromagnetic force to a pair of magnetic materials among the plurality of magnetic material pairs disposed at a position corresponding to a reaction channel of the microchip for analyzing fluids; and applying electromagnetic force to another pair of magnetic materials closest to the pair of magnetic materials.

According to an aspect of the present invention, the magnetic force application part may further include a second magnetic force application part that is different from the first magnetic force application part and is disposed at a position corresponding to a detection channel of the microchip for analyzing fluids, and the applying of electromagnetic force to the magnetic force application part may include applying electromagnetic force to the second magnetic force application part to capture complexes of the detection target antigen and magnetic particles in the microchip for analyzing fluids, i.e., immune complexes.

According to another aspect of the present invention, the plurality of second magnetic force application parts may be present in the detector and may be disposed to correspond to at least one surface of upper and lower surfaces of the detection channel of the microchip for analyzing fluids, and the applying of electromagnetic force to the magnetic force application part may further include applying electromagnetic force only to the second magnetic force application parts disposed to correspond to at least one surface of upper and lower surfaces such that the immune complexes are captured on the least one surface; and applying electromagnetic force only to the second magnetic force application parts corresponding to the other surface such that the magnetic particles floating in the detection channel migrate to the other surface.

According to another aspect of the present invention, the applying of electromagnetic force to the magnetic force application part may further include completely blocking electromagnetic force of the second magnetic force application parts such that the floating magnetic particles exit the detection channel, after applying electromagnetic force only to the second magnetic force application parts corresponding to the other surface.

Advantageous Effects

The present invention can detect a trace amount of detection target substance from a trace amount of fluid sample using an immune response between antibody-attached magnetic particles and detection target substances.

More particularly, the present invention provides magnetic particles having an optically countable size without self-assembly due to a non-specific immune response, thus providing a microchip for analyzing fluids capable of optically performing quantitative analysis of a detection target substance even without use of a fluorescent substance.

In addition, the present invention provides a method of quantitating a specific antigen using the microchip for analyzing fluids according to an embodiment of the present invention, thus being capable of detecting a trace amount of detection target substance with high sensitivity.

Effects according to the present invention are not limited by those exemplified above, and more various effects are included in the present specification.

DESCRIPTION OF DRAWINGS

FIG. 2 illustrates a procedure for quantitative analysis of an antigen using a microchip for analyzing fluids according to an embodiment of the present invention and a method of quantitating an antigen according to another embodiment of the present invention.

FIG. 3C to 3G illustrate plan views of a reaction channel of a microchip for analyzing fluids according to an embodiment of the present invention and enlarged views of a main part for illustrating a process of detecting a detection target substance in the reaction channel.

MODES OF THE INVENTION

Figure 1A:
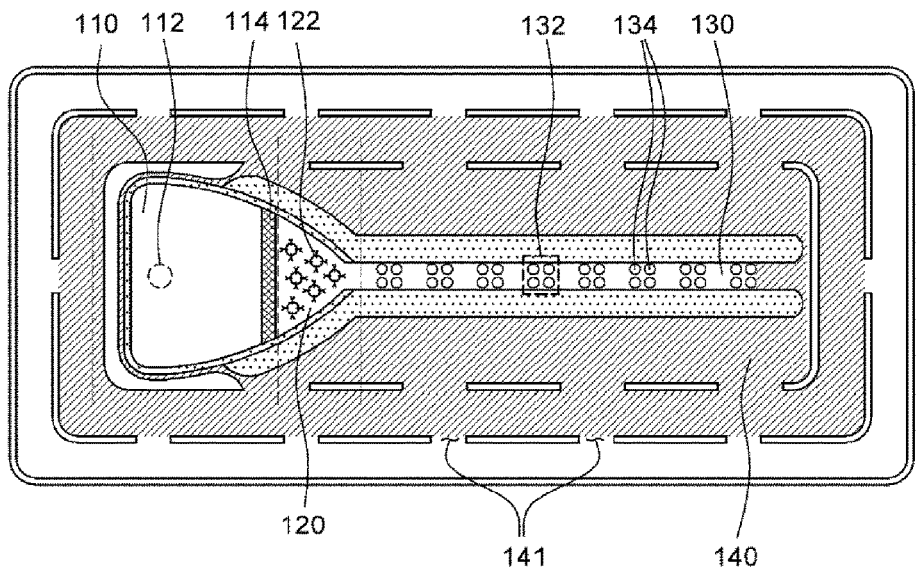
FIG. 1A is a plan view schematically illustrating a microchip for analyzing fluids according to an embodiment of the present invention.

The attached drawings for illustrating exemplary embodiments of the present invention are referred to in order to gain a sufficient understanding of the present invention, the merits thereof, and the objectives accomplished by the implementation of the present invention. The invention may, however, be embodied in many different forms and should not be construed as being limited to the embodiments set forth herein; rather, these embodiments are provided so that this disclosure will be thorough and complete, and will fully convey the concept of the invention to one of ordinary skill in the art. Meanwhile, the terminology used herein is for the purpose of describing particular embodiments and is not intended to limit the invention.

The shapes, sizes, ratios, angles, numbers, and the like disclosed in drawings for describing embodiments of the present invention are exemplary, and thus, the present invention is not limited to the illustrated particulars. In addition, in the following description of the present invention, a detailed description of known functions and configurations incorporated herein will be omitted when it may make the subject matter of the present invention unclear. In expressions "comprise", "have", "consist of" and the like mentioned in the present specification, other parts may be added unless 'only' is used. Singular forms "a," "an" and "the" are intended to include the plural forms as well, unless the context clearly indicates otherwise.

In interpreting components, it is interpreted to include error ranges even if there is no separate description.

Each of the features of the various embodiments of the present invention may be combined with each other in part or in whole, various interlocking and driving are allowed as can be understood by those skilled in the art, and each of embodiments may be implemented independently or together in combined forms.

For clarity of interpretation of the present specification, the terms used herein will be defined below.

Inside a microchip for analyzing fluids according to an embodiment of the present invention, channels, in which fluid communicates, may be formed by a body constituted of an upper surface and a lower surface.

The term "channels" used in the present specification may refer to microchannels formed between an upper surface and lower surface of a body. The microchip for analyzing fluids according to an embodiment of the present invention includes a plurality of channels. The channels may be divided into and designated as an input channel, a reaction channel, and a detection channel according to functions thereof, but the channels may be referred to as a single channel which through fluid communicates.

The lower surface may be configured such that the channels respectively have different heights to facilitate the flow of fluid. Accordingly, the channels respectively have different capacities (or volumes).

The term "assay sample" used in the present specification may refer to a sample including a detection target substance. Preferably, an assay sample may be a fluid sample. For example, an assay sample may be a cell lysate, whole blood, plasma, serum, saliva, ocular fluid, cerebrospinal fluid, sweat, urine, milk, ascites fluid, synovial fluid and peritoneal fluid, but the present invention is not limited thereto. Further, a detection target substance may be an antigen or a nuclear protein that acts as an antigen. However, a detection target substance may be easily selected by a user according to the use purpose of a microchip for analyzing fluids according to an embodiment of the present invention.

For example, when a respiratory infectious disease test is to be performed using the microchip for analyzing fluids according to an embodiment of the present invention, a detection target substance may be an antibody against influenza A, influenza B, respiratory syncytial virus (RSV), parainfluenza virus-1, parainfluenza virus-2, parainfluenza virus-3, adenovirus, human metapneumovirus (hMPV) or rhinovirus (1, 2). In addition, when an allergy test is to be performed using the microchip for analyzing fluids according to an embodiment of the present invention, a detection target substance may be IL-1 beta, IL-10, IL-2, IL-4, IL-5, IL-6, IL-71, IFN gamma, TNF-α or GM-CSF. Further, when an acute myocardial infarction diagnostic test is to be performed using the microchip for analyzing fluids according to an embodiment of the present invention, a detection target substance may be troponin I, BNP, high-sensitivity (hs) CRP, CK-MB, D-dimer, or myoglobin. Furthermore, when a sexually transmitted disease test is to be performed using the microchip for analyzing fluids according to an embodiment of the present invention, a detection target substance may be human immunodeficiency virus (HIV), chlamydia bacteria, *Treponema pallidum*, gonococcus (*Neisseria gonorrhoeae*), or human papilloma virus (HPV). When a prostate cancer test is to be performed using the microchip for analyzing fluids according to an embodiment of the present invention, a detection target substance may be a prostate specific antigen (PSA). In addition, when an immunity test of a transplantation patient is to be performed using the microchip for analyzing fluids according to an embodiment of the present invention, a detection target substance may be a BK virus or cytomegalovirus (CMV) antigen. However, the present invention is not limited to those listed above, and various antigens may be considered as a detection target substance.

Optionally, an assay sample may be lysed before being introduced into the microchip for analyzing fluids according to an embodiment of the present invention, depending upon the type of assay sample.

The term "fluid" used in the present specification may refer to a liquid or gas state or an intermediate state thereof. Such fluids may have freely flowing properties. For example, a fluid-type assay sample may flow from an input channel of the microchip for analyzing fluids according to an embodiment of the present invention to a detection channel thereof.

The term "through hole" used in the present specification refers to a hole formed to penetrate from an upper surface of the microchip for analyzing fluids according to an embodiment of the present invention to the outside. For example, an assay sample may be injected through a through hole formed in the microchip for analyzing fluids according to an embodiment of the present invention.

The term "antigen" used in the present specification refers to a substance that responds to an antibody eliciting an immune response. For example, in the microchip for analyzing fluids according to an embodiment of the present invention or a method of quantitating an antigen according to another embodiment of the present invention, an antigen may be a detection target antigen. Further, in the case of confirming the infection of a specific virus, an antigen may be a nuclear protein of virus, but the present invention is not limited thereto. An antigen may be any substances in an assay sample which are capable of immunoreacting with an antibody in the microchip for analyzing fluids according to an embodiment of the present invention.

The term "antibody" used in the present specification refers to a substance inducing a specific immune response to an antigen so as to inactivate an antigen such as virus or bacteria and fight microorganisms that have invaded the body. Further, monoclonal antibodies, which are antibodies produced by single antibody-forming cells, refer to antibodies having uniform primary structures (amino acid sequences), and polyclonal antibodies refer to a population of antibodies having heterogeneous primary structures. For example, a first antibody, which is immobilized on magnetic particles, present in the microchip for analyzing fluids according to an embodiment of the present invention may be a monoclonal antibody that recognizes only one determinant of a detection target antigen. Accordingly, the efficiency of a first antigen-antibody reaction with a detection target antigen present in a trace amount may increase. Further, a second antibody immobilized on a detection channel in the microchip for analyzing fluids according to an embodiment of the present invention may be a polyclonal antibody capable of recognizing a plurality of determinants of a detection target antigen which form immune complexes with magnetic particles. Accordingly, the efficiency of a second antigen-antibody reaction between an immune complex and the second antibody may be increased. Here, the first antibody and the second antibody may be different from fluorescence-labeled antibodies.

The term "fluorescence-labeled antibody" used in the present specification refers to a pigment (fluorochrome)-bonded label antibody that generates fluorescence by light stimulation. A fluorescent pigment may be generally a pigment protein of fluorochromic isothiocyanate (FITC), rhodamine isothiocyanate (RITC) emitting red fluorescence, or phycoerythrin. In the case of conventional microchips for analyzing fluids, use of a fluorescence-labeled antibody may be necessary to identify a detection target antigen. For example, in conventional microchips for analyzing fluids, an antigen-antibody reaction between a fluorescence-labeled antibody and a detection target antigen may occur. Accordingly, in the case of conventional microchips for analyzing fluids, a signal of a fluorescence-labeled antibody that has been subjected to an antigen-antibody reaction is observed using fluorescence antibodies, flow cytometry, and immunofluorescence, thereby indirectly confirming a detection target antigen.

Meanwhile, the microchip for analyzing fluids according to an embodiment of the present invention may detect and identify a detection target antigen using first and second antibodies different from a fluorescence-labeled antibody. For example, the microchip for analyzing fluids according to an embodiment of the present invention includes magnetic particles to which the first antibody is attached, wherein a fluorescent label is not attached to the magnetic particles. An antigen-antibody reaction between a detection target antigen and magnetic particles, to which the first antibody is attached, corresponding to the detection target antigen occurs, so that immune complexes are formed and the immune complex is captured by the chip. The magnetic particles of the captured immune complexes may be optically counted using a detector. Accordingly, detection and quantitative analysis of a detection target antigen are possible.

The term "immune complexes" used in the present specification refers to complexes bound by a first antigen-antibody reaction between the first antibody attached to magnetic particles and a detection target antigen.

The term "first antigen-antibody reaction" used in the present specification refers to an immune response between a detection target antigen and the first antibody immobilized on magnetic particles. Further, "second antigen-antibody reaction" refers to an immune response between a detection target antigen in an immune complex and the second antibody.

The term "linker molecule" used in the present specification refers to a molecule that connects a plurality of components to each other. For example, the second antibody may be immobilized in wells of a detection channel through a linker molecule. The second antibody immobilized in wells through a linker molecule may have higher fluidity than the second antibody otherwise. In addition, the density of the second antibody immobilized in wells may also be controlled by a linker molecule. Here, the linker molecule may be preferably a protein A/G, dextran or polyethylene glycol (PEG), but the present invention is not limited thereto.

The term "magnetic particles" used in the present specification refers to particles having magnetic properties. Magnetic particles may be detachably arranged in the microchip for analyzing fluids according to an embodiment of the present invention. For example, magnetic particles may be attached in a lyophilized state to a reaction initiation channel of the microchip for analyzing fluids according to an embodiment of the present invention and may be detached according to the flow of a fluid-type assay sample.

Further, magnetic particles may be optically counted and may have a size where nonspecific self-assembly does not occur. For example, when a particle diameter of the magnetic particles is 0.1 to 6.0 μm, the magnetic particles may be optically counted by a detector even if the first antibody or the second antibody is not a fluorescence-labeled antibody. Further, magnetic particles having a particle diameter of 0.1 to 6.0 μm have a lower probability of nonspecific self-assembly than magnetic particles having a particle diameter of 0.1 μm or less.

The shape of the magnetic particles is not limited so long as they can be rolled in the microchip for analyzing fluids according to an embodiment of the present invention.

The term "flow control pillars" used in the present specification may be used to refer to any structures that induce uniform flow of a fluid-type assay sample in the microchip for analyzing fluids according to an embodiment of the present invention. For example, a plurality of flow control pillars may be disposed inside the microchip for analyzing fluids according to an embodiment of the present invention and may function to cause a fluid-type assay sample to have a uniform movement pattern. Here, the flow control pillars may have a particle diameter of 45 to 70 μm and may be disposed on an upper surface, but the present invention is not limited thereto.

The term "wells" used in the present specification refers to holes formed in an upper or lower surface of the microchip for analyzing fluids according to an embodiment of the present invention. For example, a plurality of wells may be formed in the detection channel of the microchip for analyzing fluids according to an embodiment of the present invention. Here, wells may include the second antibody and have a particle diameter of 1.2 times to 2 times the size of the magnetic particles such that only one immune complex is captured.

Meanwhile, the term "capture pillars" used in the present specification refers to pillars formed in an upper or a lower surface of the microchip for analyzing fluids according to an embodiment of the present invention and may be used for purposes similar to those of the wells described above. For example, a plurality of capture pillars may be formed in the detection channel of the microchip for analyzing fluids according to an embodiment of the present invention. Here, the second antibody may be immobilized between the capture pillars, and the capture pillars may be arranged at an interval of 1.2 to 2 times the size of the magnetic particles such that only one immune complex is captured.

The capture pillars may have a function different from that of the flow control pillars in the microchip for analyzing fluids according to an embodiment of the present invention.

The term "magnetic material" used in the present specification may refer to any material capable of forming magnetism with magnetic particles in the microchip for analyzing fluids according to an embodiment of the present invention, outside the microchip. For example, the magnetic material may be included in a detector so as to promote the first antigen-antibody reaction in the reaction channel of the microchip for analyzing fluids according to an embodiment of the present invention or identify an immune complex captured in the detection channel thereof. In particular, the magnetic material may be an electromagnet in which magnetization is controlled according to the flow of current, and the microchip for analyzing fluids according to an embodiment of the present invention may be introduced between two electromagnets disposed in a detector. As the magnetic force of the two electromagnets is controlled, a nonspecific immune complex or magnetic particles, which do not react with a detection target antigen, in the microchip for analyzing fluids according to an embodiment of the present invention may be washed. Accordingly, it is possible to detect a detection target antigen with high accuracy.

Meanwhile, the term "magnetic force application part" used in the present specification may have the same meaning as "magnetic material" described above. For example, the detector may also include a magnetic force application part. The magnetic force application part may include a first magnetic force application part constituted of a plurality of magnetic material pairs and disposed at a position corresponding to the reaction channel of the microchip for analyzing fluids; and a second magnetic force application part different from the first magnetic force application part and disposed at a position corresponding to the detection channel of the microchip for analyzing fluids. Here, the magnetic force application parts may have various shape so long as they can apply electromagnetic force to the reaction channel or the detection channel.

The term "quantitative analysis" used in the present specification refers to an assay that clarifies a quantitative relationship that constitutes a substance. According to another embodiment of the present invention, a method of quantitating an antigen is provided. For example, in accordance with the method of quantitating an antigen according to another embodiment of the present invention using the microchip for analyzing fluids according to an embodiment of the present invention, a detection target antigen may be detected and quantitatively analyzed by counting magnetic particles captured in the detection channel.

The term "CMOS image sensor" used in the present specification refers to a low power consumption-type image sensing device having the structure of a complementary metal oxide semiconductor. A CMOS image sensor may be used in a detector that is used for the microchip for analyzing fluids according to an embodiment of the present invention. For example, when the microchip for analyzing fluids according to an embodiment of the present invention is introduced into a CMOS image sensor-based detector, a captured immune complex may be recognized by the CMOS image sensor.

Hereinafter, the microchip for analyzing fluids according to an embodiment of the present invention is described in detail with reference to FIGS. 1A to 1F.

FIG. 1A is a plan view schematically illustrating the microchip for analyzing fluids according to an embodiment of the present invention. Referring to FIG. 1A, a microchip 100 for analyzing fluids may include a plurality of channels 110, 120, 130, and 140 formed between an upper surface and a lower surface thereof. Further, inside the microchip 100 for analyzing fluids, a plurality of through holes 141 may be formed on sides of the microchip 100 such that fluid moves in one direction by osmotic pressure. In addition, the through holes 141 maintain the capillary force by maintaining the air pressure such that an assay sample sufficiently flows to the flow retention channel 140.

The plurality of channels includes an input channel 110, a reaction channel 120, and a detection channel 130. In particular, the input channel 110 is configured to input an assay sample through the through hole 112 penetrating the upper surface. The reaction channel 120 is configured to be in fluid communication with the input channel 110. The reaction channel 120 includes the assay sample flowing from the input channel 110; and magnetic particle-first antibody complexes 122 to be subjected to the first antigen-antibody reaction.

In addition, the reaction channel 120 is configured to have a height higher than a lower surface forming the input channel 110. The detection channel 130 is configured to be in fluid communication with the reaction channel 120. In the detection channel 130, the second antibody to be subjected to the second antigen-antibody reaction with the immune complexes flowing from the reaction channel 120 is immobilized. In addition, the detection channel 130 has a longer length and a narrower width than the input channel 110 or the reaction channel 120.

The input channel 110 may further include a filter 114. When an assay sample 116 passes through the filter 114, components larger in size than the filter 114 among components present in the assay sample 116 may be removed. For example, when an assay sample is blood, blood cells may be removed through the filter 114. Accordingly, serum or plasma containing nuclear proteins serving as antigens may migrate to the input channel 110. Further, the filter 114 may be a filter treated with 1 M EDTA, for effective filtering. Meanwhile, the input channel 110 may have a length of 15 to 25% with respect to the entire length of the microchip 100 for analyzing fluids and may have a larger capacity than other channels. For example, the input channel 110 may be configured to accommodate substantially more than the volume of the assay sample 116 reacting in the reaction channel 120.

The magnetic particle-first antibody complexes 122 in the reaction channel 120 may be attached to the upper surface. Meanwhile, the reaction channel 120 may have a width narrower than the input channel 110 such that the assay sample 116 can smoothly move from the input channel 110 to the reaction channel 120 and may have a width that gradually decreases from the input channel 110 to the detection channel 130. In addition, the height of the lower surface may be decreased toward the detection channel 130 from a start portion of the reaction channel 120.

The detection channel 130 may include a plurality of detection parts 132 that include a plurality of wells 134. The detection parts 132 may be arranged at a series of intervals in the detection channel 130, but the present invention is not limited thereto. The detection parts 132 may have different intervals or areas or various shapes including the wells 134 therein, depending upon the type of an assay sample or a use purpose of the microchip 100 for analyzing fluids. Meanwhile, since the second antibody is immobilized in the wells 134, the second antibody is subjected to the second antigen-antibody reaction with an immune complex flowing from the reaction channel 120, thus capturing the immune complex. Meanwhile, the detection channel 130 may have a length of 40 to 60% with respect to the entire length of the microchip 100 for analyzing fluids, thus having a length longer than other channels.

Meanwhile, when an additional assay sample 116, other than a reaction volume that is substantially reacted in the reaction channel 120 and the detection channel 130, is introduced, the assay sample 116 passing through the detection channel 130 may migrate to the flow retention channel 140. As a result, the air pressure created by the through holes 141 formed in the flow retention channel 140 may maintain the flow of the assay sample 116. Accordingly, the assay sample 116 may maintain sufficient flow until all reactions in the microchip 100 for analyzing fluids are terminated. Further, along continuous flow of the assay sample 116 in the flow retention channel 140, the immune complex formed in the reaction channel 120 may effectively migrate to the detection channel 130. In addition, along such flow, non-specific immune reaction complexes or magnetic particles, which do not form immune complexes, formed in the detection channel 130 may be washed and migrate out of the detection channel 130.

Figure 1B:
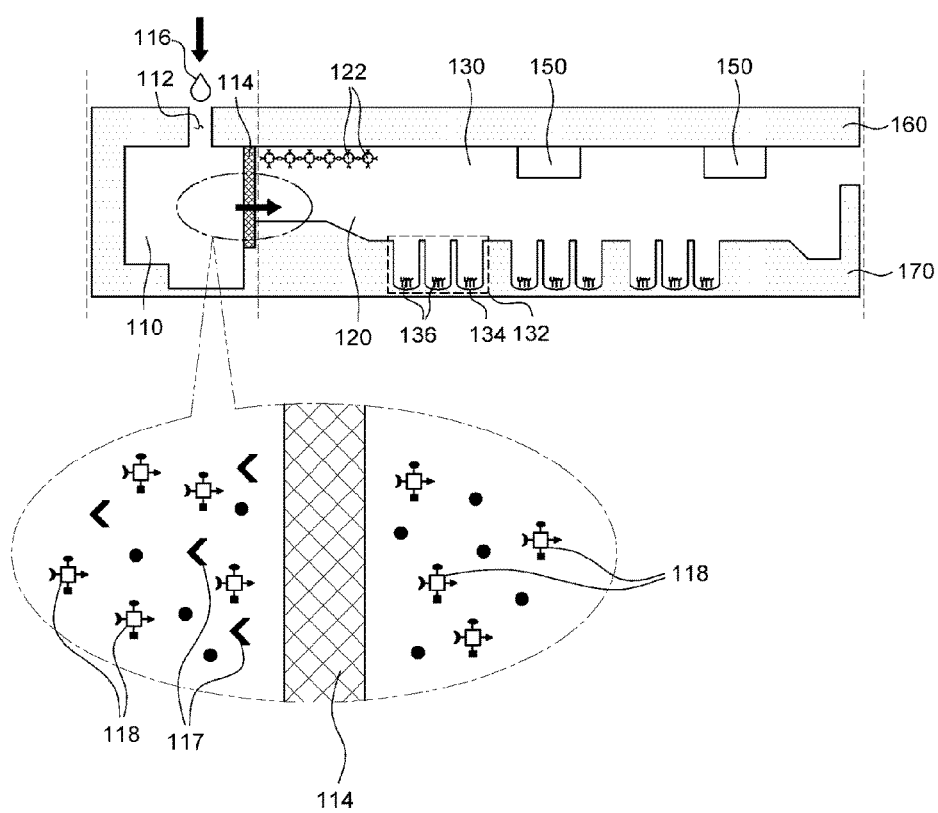
FIGS. 1B to 1D are schematic side views of a microchip for analyzing fluids according to an embodiment of the present invention and enlarged views of a main part for schematically illustrating a process of detecting a detection target antigen.
Figure 1C:
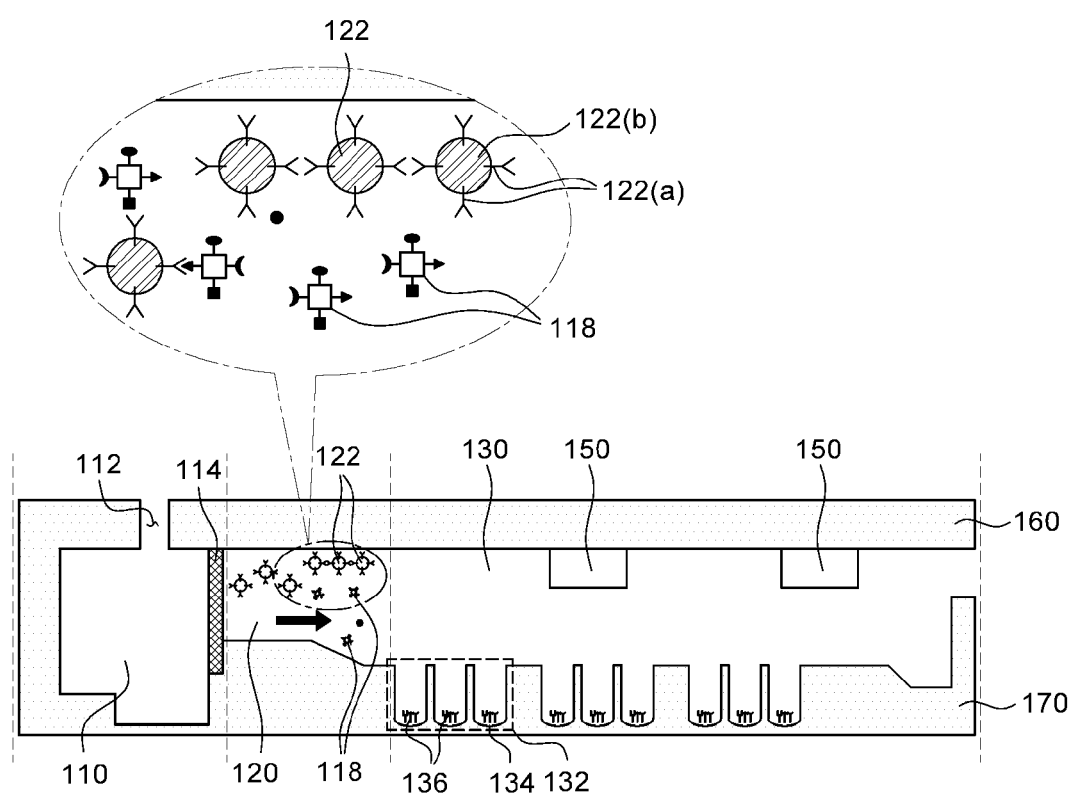
Figure 1D:
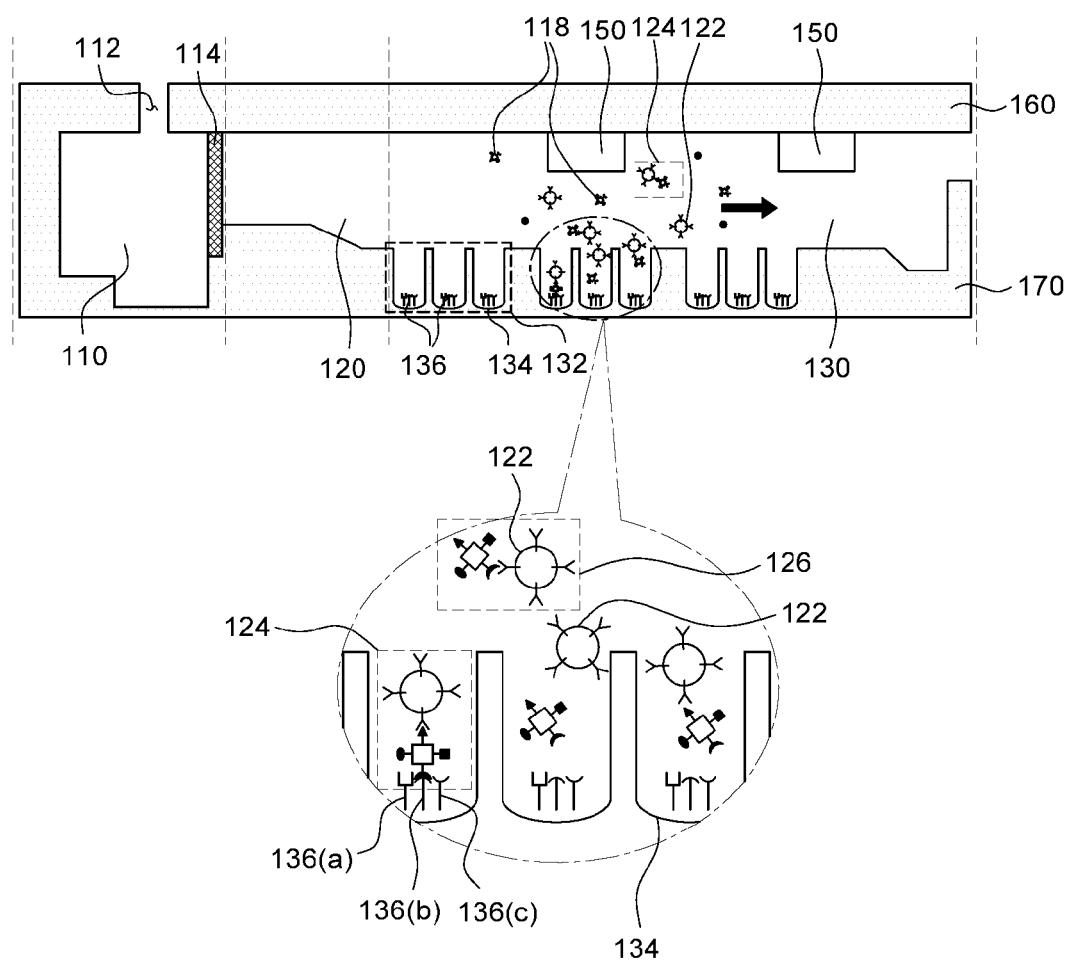
Figure 1E:
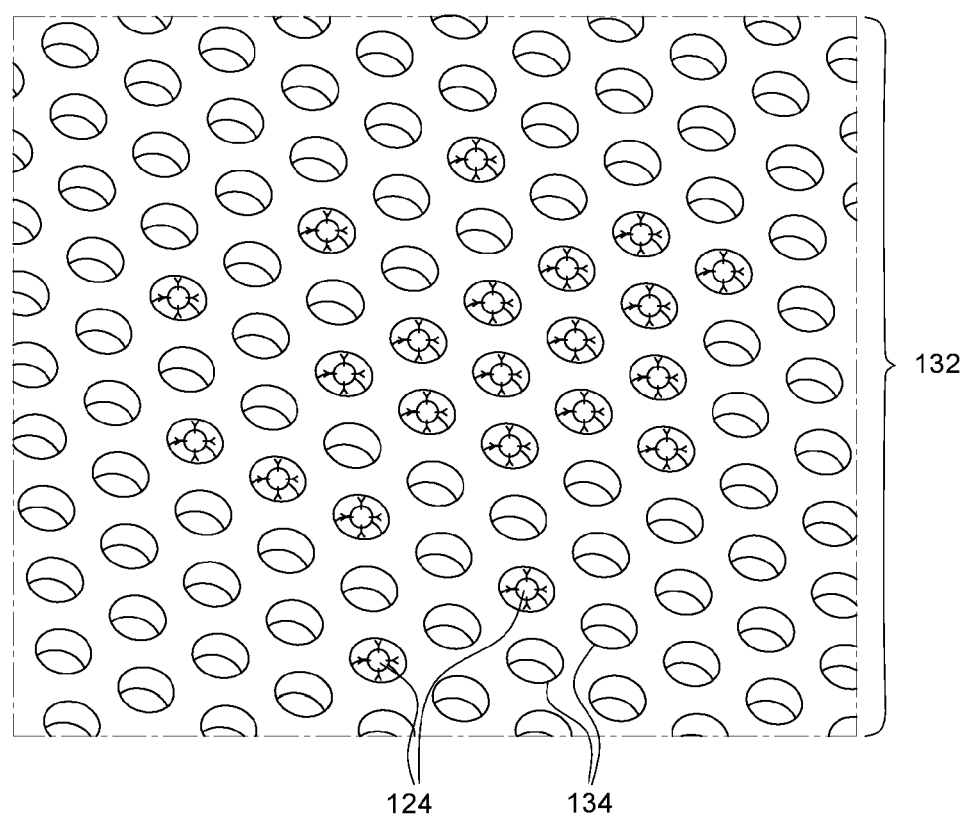
FIGS. 1E and 1F illustrate embodiments of a detection channel in a microchip for analyzing fluids according to an embodiment of the present invention.
Figure 1F:
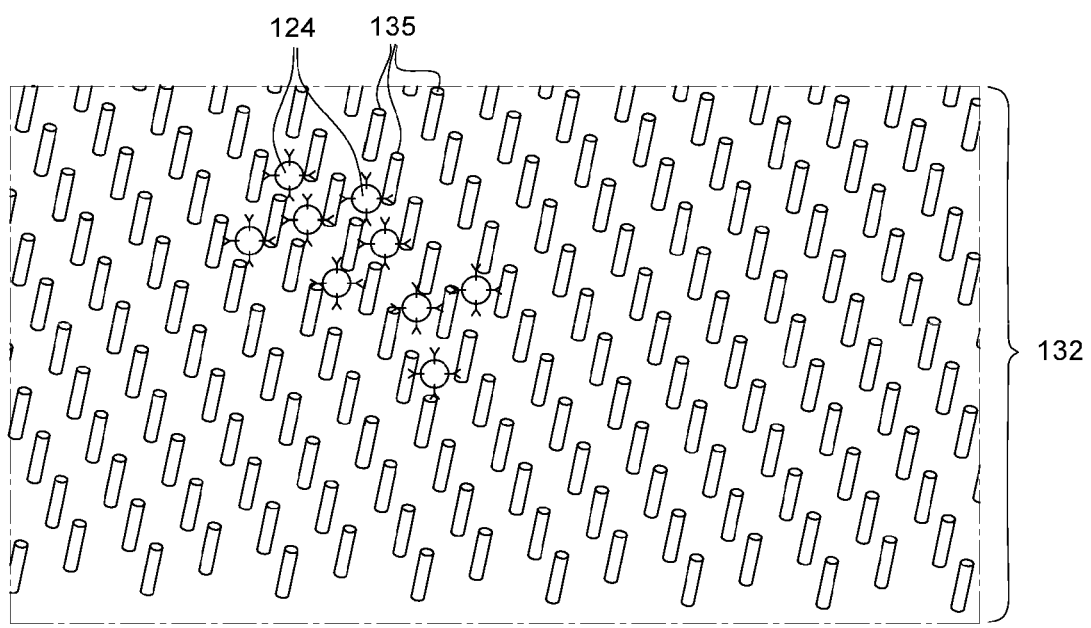

FIGS. 1B to 1D are schematic side views of the microchip for analyzing fluids according to an embodiment of the present invention and enlarged views of a main part for schematically illustrating a process of detecting a detection target antigen. FIGS. 1E and 1F illustrate embodiments of a detection channel in the microchip for analyzing fluids according to an embodiment of the present invention.

Referring to FIG. 1B, the assay sample 116 may be injected into the input channel 110 through an inlet 112. Here, the assay sample 116 may be injected into the input channel 110, optionally, after being lysed. The assay sample 116 may also include blood cells 117 and detection target antigens 118. Here, by the filter 114 in the input channel 110, blood cells 117 larger than a pore size of the filter 114 may be filtered out, and detection target antigens 118 in serum or plasma may flow to the reaction channel 120.

Referring to FIG. 1C, the detection target antigens 118 in the assay sample 116 and the magnetic particle-first antibody complexes 122 attached to an upper surface 160 are bound to each other by an antigen-antibody immune response. In addition, before and after binding, the first antibody complexes may be detached by fluid components. In terms of detachment of the magnetic particle-first antibody complexes 122, the body including the upper surface 160 is preferably made of a hydrophobic material, but the present invention is not limited thereto. For example, when the upper surface 160 is made of a hydrophobic material such as bovine serum albumin (BSA) or fetal bovine serum (FBS), a contact area between the magnetic particle-first antibody complexes 122 and the upper surface 160 is decreased, resulting in easy detachment.

Meanwhile, each of the magnetic particle-first antibody complexes 122 is particularly composed of first antibodies 122 (*a*) and a magnetic particle 122 (*b*). Here, the first antibodies 122 (*a*) may be a monoclonal antibody so as to increase the accuracy of an immune response with trace amounts of the detection target antigens 118. Further, the magnetic particle-first antibody complexes 122 may be attached in a lyophilized state to the upper surface 160, but the present invention is not limited thereto. In the reaction channel 120, the first antigen-antibody reaction between detached magnetic particle-first antibody complexes 122 and the detection target antigens 118 may occur.

Preferably, the magnetic particle 122 (b) may have a particle diameter of 0.1 to 6.0 µm. More preferably, the magnetic particle 122 (b) may have a particle diameter of 1.0 to 4 µm. For example, when a particle diameter of the magnetic particle 122 (b) is 1.0 to 4 µm, the first antibodies 122 (a) may be optically counted by a detector even if the first antibodies 122 (a) is not an antibody labeled with a fluorescent substance, i.e., a fluorescence-labeled antibody. Further, when the magnetic particle 122 (b) has a particle diameter of 1.0 to 4 µm, the probability of nonspecific self-assembly may be low, compared to a magnetic particle 122 (b) having a particle diameter of 1.0 µm or less. In addition, when the magnetic particle 122 (b) has a particle diameter of 4 µm or larger, the efficiency of an antigen-antibody reaction may be low, compared to a magnetic particle 122 (b) having a particle diameter of 1.0 to 4 µm.

Meanwhile, in the first antigen-antibody reaction, it may be preferred to use the magnetic particle-first antibody complexes 122 to which the first antibodies 122 (a) are attached in a number of $1*10^5$ to $4*10^5$ times a surface area of the magnetic particle 122 (b), but the present invention is not limited thereto. Further, when the reaction channel 120 in the microchip 100 for analyzing fluids is introduced to a detector including a magnetic material, the efficiency of the first antigen-antibody reaction may increase. For example, dispersion force of the magnetic particle-first antibody complexes 122 may be controlled by the magnetic material in the detector and, as a result, self-aggregation of the magnetic particle-first antibody complexes 122 may be decreased.

Further, flow control pillars 150 may be formed on the upper surface 160 forming a plurality of channels. In particular, the flow control pillars 150 formed in the reaction channel 120 may physically regulate the flow of flowing magnetic particle-first antibody complexes 122. Accordingly, sufficient time for an immune response between the first antibodies 122 (a) and the detection target antigens 118 is allowed in the reaction channel 120, so that the efficiency of the first antigen-antibody reaction may increase. The flow control pillars 150 may be attached to a lower surface 170 as desired. Further, the flow control pillars 150 may have a diameter of 50 to 70 µm.

Referring to FIG. 1D, immune complexes 124 formed by the first antigen-antibody reaction in the reaction channel 120 may flow from the reaction channel 120 to the detection channel 130. Here, a second antibody 136 may be immobilized in the detection channel 130. Meanwhile, the second antibody 136 may be immobilized via a linker in a plurality of wells 134 formed in the detection channel 130. In particular, the plurality of wells 134 may include the immune complexes 124 captured by the second antigen-antibody reaction with the second antibody 136 (see FIG. 1E). Here, the diameter and depth of each of the wells 134 may be 1.2 to 2 times a particle diameter of the magnetic particle 122 (b), preferably 1.2 to 2 times the size of each of the magnetic particle-first antibody complexes 122. For example, when the wells 134 have a size of 1.2 times or less the magnetic particle-first antibody complexes 122, it is undesirable to capture the magnetic particle-first antibody complexes 122. On the other hand, when the wells 134 have a size of 2 times or more the magnetic particle-first antibody complexes 122, two magnetic particle-first antibody complexes 122 may be contained in each of the wells 134, which is undesirable. Further, the respective wells 134 may be arranged at an interval of 5 to 8 µm on the lower surface 170, but the present invention is not limited thereto.

Meanwhile, the number of the wells 134 in the detection channel 130 may depend upon the capacity of a reaction channel 110, the concentration of the assay sample 116, or a dissociation constant of the assay sample 116. In particular, the dissociation constant may be related to the binding affinity between the detection target antigens 118 in the assay sample 116 and the first antibodies 122 (a) or the second antibody 136 and, accordingly, may be related to the number of the wells 134 that may include the second antibody 136.

For example, the number of the wells 134 is proportional to the capacity of the reaction channel 110 and the concentration or dissociation constant of the assay sample 116 and, accordingly, may be calculated by Equation 1:

Number of wells=volume of reaction channel×concentration of assay sample (or dissociation constant of assay sample)×6.23×10²³  [Equation 1]

Here, the volume of the reaction channel 110 is the capacity of the assay sample 116 and, thus, may correspond to the volume of an added assay sample 116. In addition, Avogadro's number ($6.23 \times 10^{23}$) is a formula set in consideration of the number of particles in 1 mole of the assay sample 116.

As a particular example, when the concentration of the assay sample 116 is 100 fM (or 0.1 pM) and the volume of the reaction channel 110 is 1 µl, the number of the wells 134 in the detection channel 130 is preferably 60,000 according to [Equation 1], as summarized in Table 1. When the assay sample 116 is used at the same concentration, i.e., 100 fM and the volume of the reaction channel 110 is 2.5 µl, the number of the wells 134 is preferably 150,000. That is, the number of the wells 134 may be proportional to the volume of the reaction channel 110.

[Amendment under Rule 26, Jul. 8, 2017]

TABLE 1

| Concerstration of assay sample (fM) | Volume of reactor (µg) | | | | |
| --- | --- | --- | --- | --- | --- |
| | 1 | 2.5 | 5 | 10 | 100 |
| 0.001 | 1 | 2 | 3 | 6 | 60 |
| 0.01 | 6 | 15 | 30 | 60 | 600 |
| 0.1 | 60 | 150 | 300 | 600 | 6,000 |
| 1 | 600 | 1,500 | 3,000 | 6,000 | 60,000 |
| 10 | 6,000 | 15,000 | 30,000 | 60,000 | 600,000 |
| 100 | 60,000 | 150,000 | 300,000 | 600,000 | 6,000,000 |

TABLE 1-continued

| Concerstration of assay sample (fM) | Volume of reactor (μg) | | | | |
|---|---|---|---|---|---|
| | 1 | 2.5 | 5 | 10 | 100 |
| 1000 | 600,000 | 1,500,000 | 3,000,000 | 6,000,000 | 60,000,000 |
| 10000 | 6,000,000 | 15,000,000 | 30,000,000 | 60,000,000 | 600,000,000 |
| 100000 | 60,000,000 | 150,000,000 | 300,000,000 | 600,000,000 | 6,000,000,000 |
| 1000000 | 600,000,000 | 1,500,000,000 | 3,000,000,000 | 6,000,000,000 | 60,000,000,000 |
| 10000000 | 6,000,000,000 | 15,000,000,000 | 30,000,000,000 | 60,000,000,000 | 600,000,000,000 |

Accordingly, the number of the wells 134 in the microchip 100 for analyzing fluids according to an embodiment of the present invention may be determined depending upon the concentration of the assay sample 116 or the dissociation constant thereof and the volume of the reaction channel 110.

Optionally, a plurality of capture pillars 135, instead of the plurality of wells 134, may be formed on the lower surface 170 of the detection channel 130 (see FIG. 1F). In particular, when the plurality of capture pillars 135 is formed in the detection channel 130 so as to capture the immune complexes 124, the second antibody may be immobilized between the capture pillars 135. Further, the capture pillars 135 may be arranged at an interval of 1.2 times to 2 times the size of the magnetic particle 122 (b), preferably the immune complexes 124, such that only one immune complex 124 is captured in each of the capture pillars 135.

The second antibody 136 may be a polyclonal antibody including antibodies 136 (a), 136 (b), and 136 (c) having different antigen-specific structures so as to increase the accuracy of detection. Further, when the second antibody 136 in the detection channel 130 is introduced into a detector provided with a magnetic material that is capable of attracting or repelling magnetic particles of the microchip 100 for analyzing fluids, the second antibody 136 may be located at a location corresponding to the magnetic material.

The immune complexes 124 having flowed into the detection channel 130 may be captured in the wells 134 via the second antigen-antibody reaction with the second antibody 136. In particular, in the detection channel 130, the detection target antigens 118 of the immune complexes 124 and the second antibody 136 having a structure specific to the detection target antigens 118 are bound to each other, thereby capturing the immune complexes 124. For example, when the detection channel 130 in the microchip 100 for analyzing fluids is introduced into a detector including a magnetic material, the immune complexes 124 including the detection target antigens 118 may be more accurately captured in the wells 134 and, as a result, the detection target antigens 118 may be detected. Here, to increase the detection accuracy of the immune complexes 124, the intensity of a magnetic material in the detector corresponding to the lower surface 170 to which the second antibody 136 is attached may be less than the intensity of the magnetic field of a magnetic material corresponding to the upper surface 160.

Hereinafter, a procedure of the method of quantitating an antigen according to another embodiment of the present invention is described in detail with reference to FIG. 2. Here, reference numerals used in FIGS. 1a to 1d are used to refer to components for convenience of description.

FIG. 2 illustrates a procedure for quantitative analysis of an antigen using the microchip for analyzing fluids according to an embodiment of the present invention and the method of quantitating an antigen according to another embodiment of the present invention.

Referring to FIG. 2, first, the assay sample 116 for quantitative analysis of a specific antigen is prepared (S210). Here, the assay sample 116 may be a fluid sample, preferably a sample including nuclear proteins. Optionally, in the preparation step (S210), a lysis process may be performed depending upon the type of the assay sample 116. Further, the assay sample 116 may be preferably a cell lysate, whole blood, plasma, serum, saliva, ocular fluid, cerebrospinal fluid, sweat, urine, milk, ascites fluid, synovial fluid, or peritoneal fluid, but the present invention is not limited thereto.

Next, the prepared assay sample 116 is applied to the microchip 100 for analyzing fluids according to an embodiment of the present invention (S220). For example, the assay sample 116 may be added dropwise into the inlet 112 of the microchip 100 for analyzing fluids so that the assay sample 116 is injected into the input channel 110.

Next, the microchip 110 for analyzing fluids is introduced into a detector including a magnetic force application part, made of a magnetic material, and a CMOS image sensor to apply electromagnetic force to the magnetic force application part (S230). Accordingly, specific reactions such as the first antigen-antibody reaction and the second antigen-antibody reaction occur. That is, in the step (S230) of applying specific electromagnetic force, the first antigen-antibody reaction in the reaction channel 120 and the second antigen-antibody reaction in the detection channel 130 described above with reference to FIGS. 1A to 1D occur, so that the immune complexes 124 may be captured in the detection channel 130 in the microchip 100 for analyzing fluids.

Finally, the immune complexes 124 captured in the detection channel 130 in the step (S230) of applying electromagnetic force using the CMOS image sensor in the detector are counted (S240). Here, the number of the counted immune complexes 124 may be proportional to the number of the detection target antigens 118. By the counting step (S240), the detection target antigens 118 may be quantitatively analyzed. The immune complexes 124 may be counted in a manner of detecting magnetic particles in an obtained image. When a manner of distinguishing magnetic particles having the above-described size to which the fluorescent substance is not attached is used, the manner is not specifically limited.

Hereinafter, the microchip for analyzing fluids according to an embodiment of the present invention, the antigen quantitative analysis system used in the method of quantitating an antigen according to another embodiment of the present invention, and the step (S230) of applying electromagnetic force and the counting step (S240) of FIG. 2 are described in detail with reference to FIGS. 3A, 3B to 3G, and 3H to 3K. Here, reference numerals used in FIGS. 1A to 1D and 2 are used to refer to components for convenience of description.

Figure 3A:
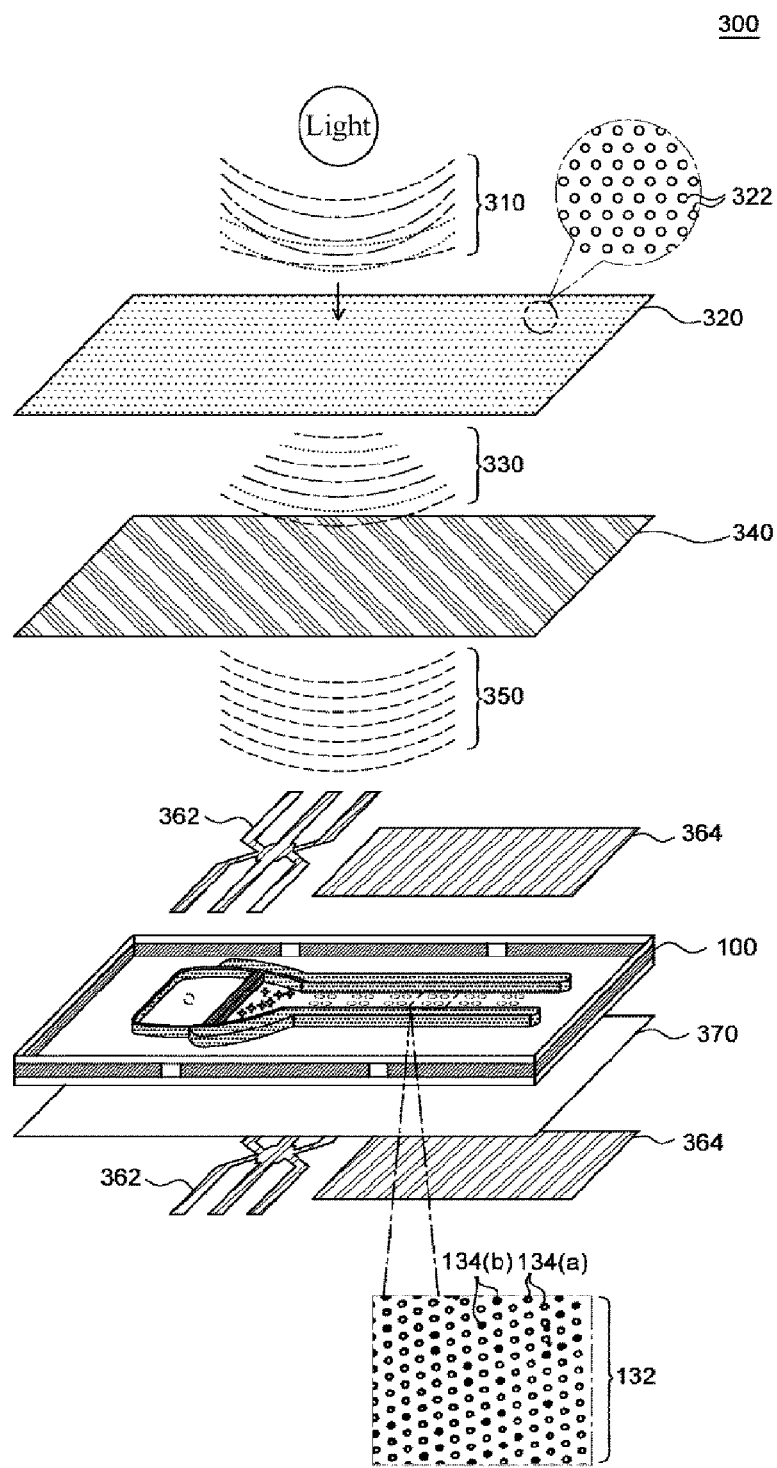
FIG. 3A is a schematic exploded perspective view illustrating the configuration of an antigen quantitative analysis system using a microchip for analyzing fluids according to an embodiment of the present invention and a method of quantitating an antigen according to another embodiment of the present invention.
Figure 3B:
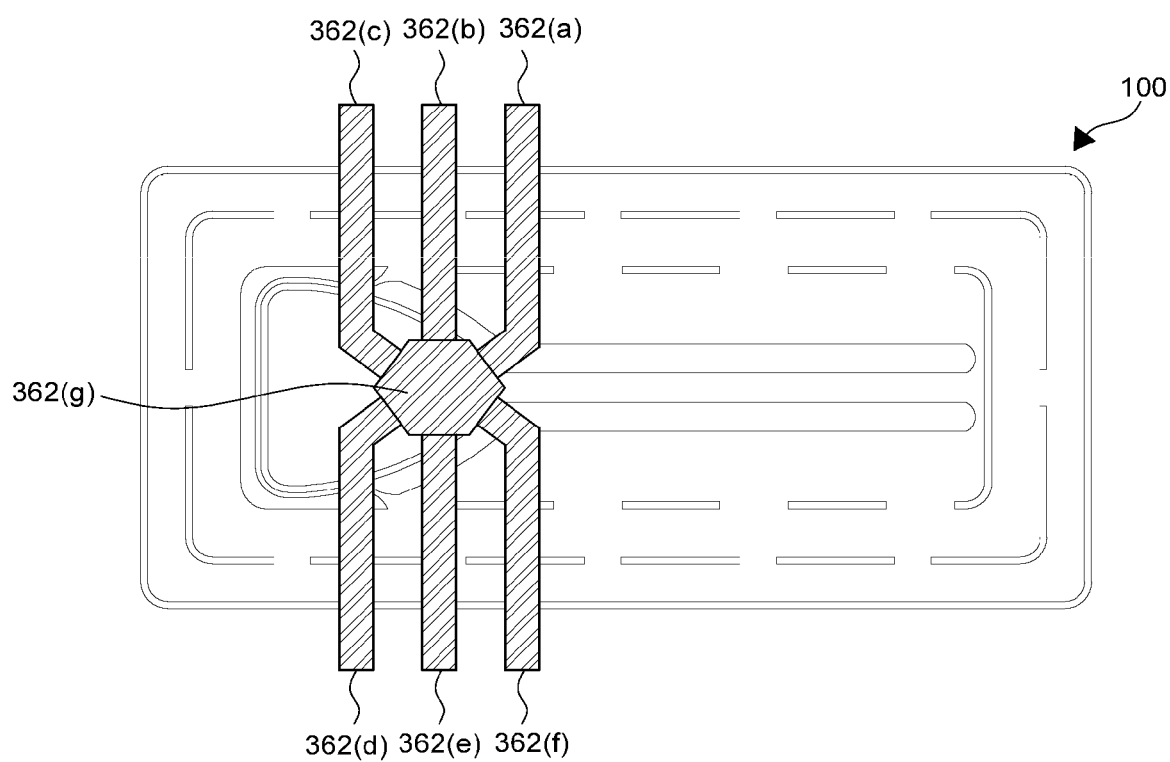
FIG. 3B is a plan view illustrating a reaction channel of a microchip for analyzing fluids according to an embodiment of the present invention and a first magnetic force application part of a detector arranged therein.

FIG. 3A is a schematic exploded perspective view illustrating the configuration of an antigen quantitative analysis system using a microchip for analyzing fluids according to an embodiment of the present invention and the method of quantitating an antigen according to another embodiment of the present invention. FIG. 3B is a plan view illustrating a reaction channel of a microchip for analyzing fluids according to an embodiment of the present invention and a first magnetic force application part of a detector arranged therein. FIG. 3C to 3G illustrate plan views of a reaction channel of a microchip for analyzing fluids according to an embodiment of the present invention and enlarged views of a main part for illustrating a process of detecting a detection target substance in the reaction channel. FIG. 3H is a plan view illustrating a detection channel of a microchip for analyzing fluids according to an embodiment of the present invention and a second magnetic force application part of a detector arranged therein. FIGS. 3I to 3K illustrate side views of a detection channel of a microchip for analyzing fluids according to an embodiment of the present invention and enlarged views of a main part for illustrating a process of detecting a detection target substance in the detection channel.

Referring to FIG. 3A, an antigen quantitative analysis system 300 includes a pinhole aperture 320, a wavelength filter 340, first magnetic force application parts 362, second magnetic force application parts 364 and a CMOS image sensor 370.

In the step (S230) of applying electromagnetic force, the microchip 100 for analyzing fluids may be introduced between the plurality of first magnetic force application parts 362 and the second magnetic force application parts 364. The CMOS image sensor 370 may be disposed between the microchip 100 for analyzing fluids and the first and second magnetic force application parts 362 and 364 disposed under the microchip 100. More particularly, the first magnetic force application parts 362 may be disposed to correspond to the reaction channel 120 in the microchip 100 for analyzing fluids, and the second magnetic force application parts 364 may be disposed to correspond to the detection channel 130 in the microchip 100 for analyzing fluids. Here, the first magnetic force application parts 362 and the second magnetic force application parts 364 may be electromagnets whose magnetic force is easily adjusted according to the flow of current, but the present invention is not limited thereto.

Referring to FIG. 3B, the first magnetic force application part 362 disposed at the reaction channel 120 includes a core magnetic material 362 (g) and protruding magnetic materials 362 (a) to 362 (f) surrounding the core magnetic materials 362 (g). However, the structure of the first magnetic force application part 362 is not limited to the illustrated shape, and may have various shapes to which electromagnetic force can be optionally applied.

Figure 3C:
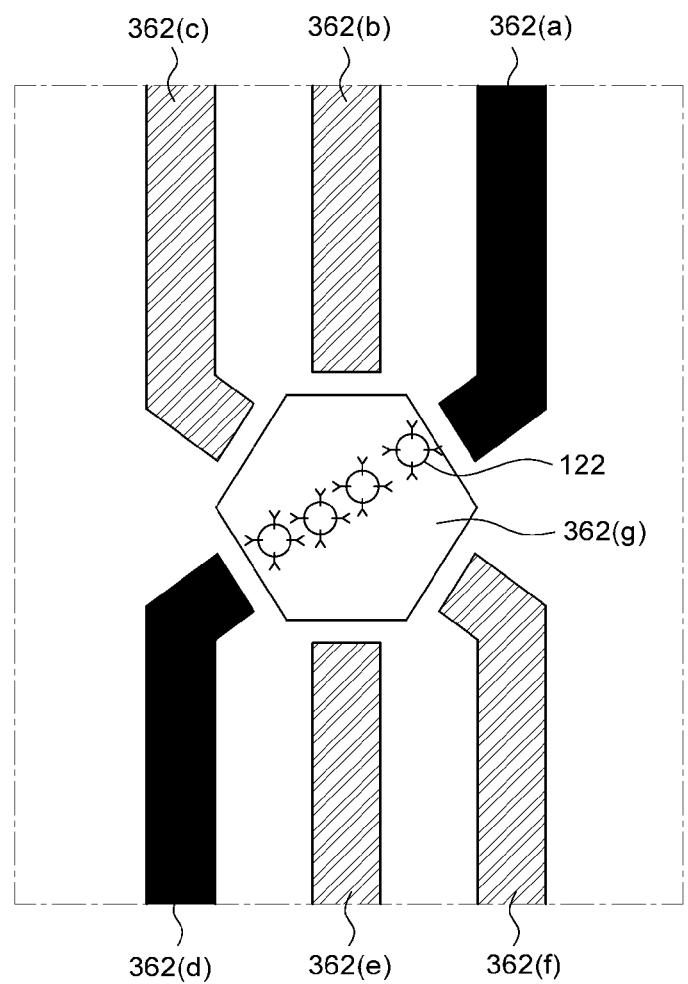
Figure 3D:
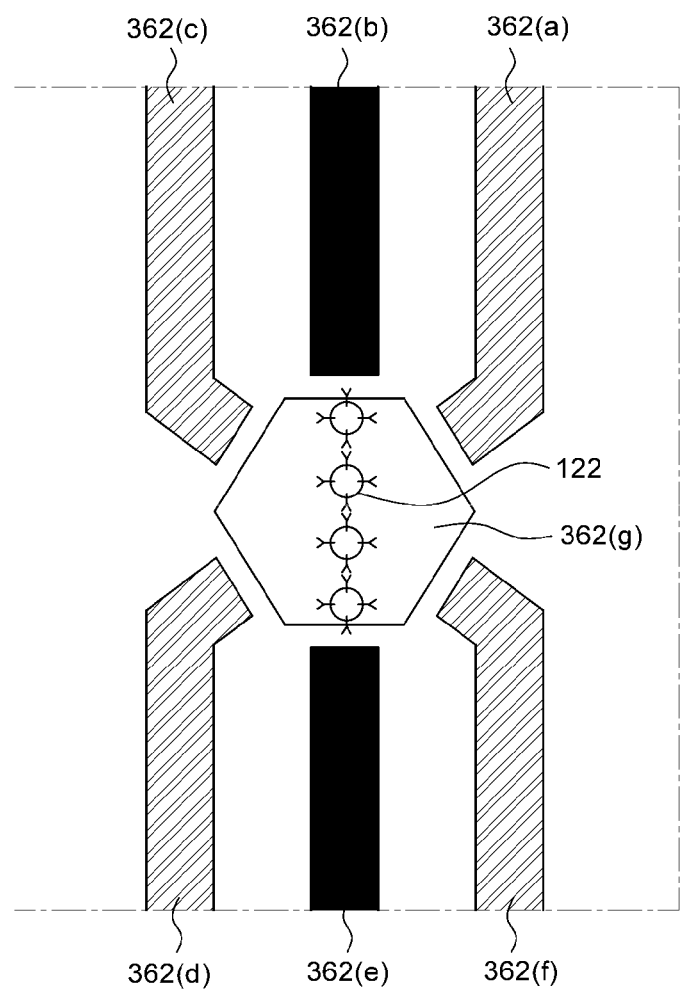
Figure 3E:
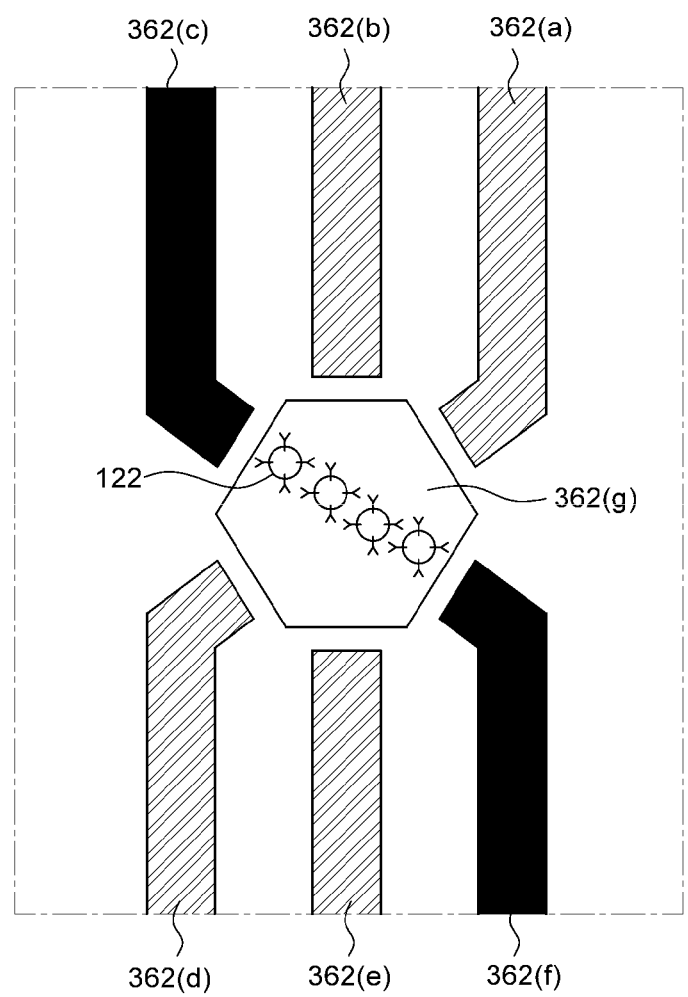

Referring to FIGS. 3C to 3E, electromagnetic force may be applied to one protruding magnetic material pair of the plurality of protruding magnetic material pairs (362 (a)) and 362 (d), 362 (b) and 362 (e), 362 (c) and 362 (f), and electromagnetic force may be applied to another protruding magnetic material pair adjacent to the electromagnetic force-applied protruding magnetic material pair. For example, electromagnetic force may only be applied to the protruding magnetic material pairs 362 (a) and 362 (d). As a result, the magnetic particle-first antibody complexes 122 may be arranged in line at a position corresponding to the core magnetic material 136 (g) between the protruding magnetic material pairs 362 (a) and 362 (d) in the reaction channel 120 (FIG. 3C). Next, electromagnetic force may only be applied to the protruding magnetic material pairs 362 (b) and 362 (e) or 362 (c) and 362 (f) that are adjacent to the protruding magnetic material pairs 362 (a) and 362 (d). As a result, the magnetic particle-first antibody complexes 122 may be arranged in line at a position corresponding to the core magnetic material 136 (g) between the protruding magnetic material pairs 362 (b) and 362 (e) or 362 (c) and 362 (f) in the reaction channel 120 (FIGS. 3D and 3E). As electromagnetic force of the protruding magnetic material pairs is sequentially adjusted in such a manner, the magnetic particle-first antibody complexes 122 may rotate in the reaction channel 120. As a result, the magnetic particle-first antibody complexes 122 may be dispersed, and the efficiency of the first antigen-antibody reaction between the detection target antigens 118 and the magnetic particle-first antibody complexes 122 may also increase.

Figure 3G:
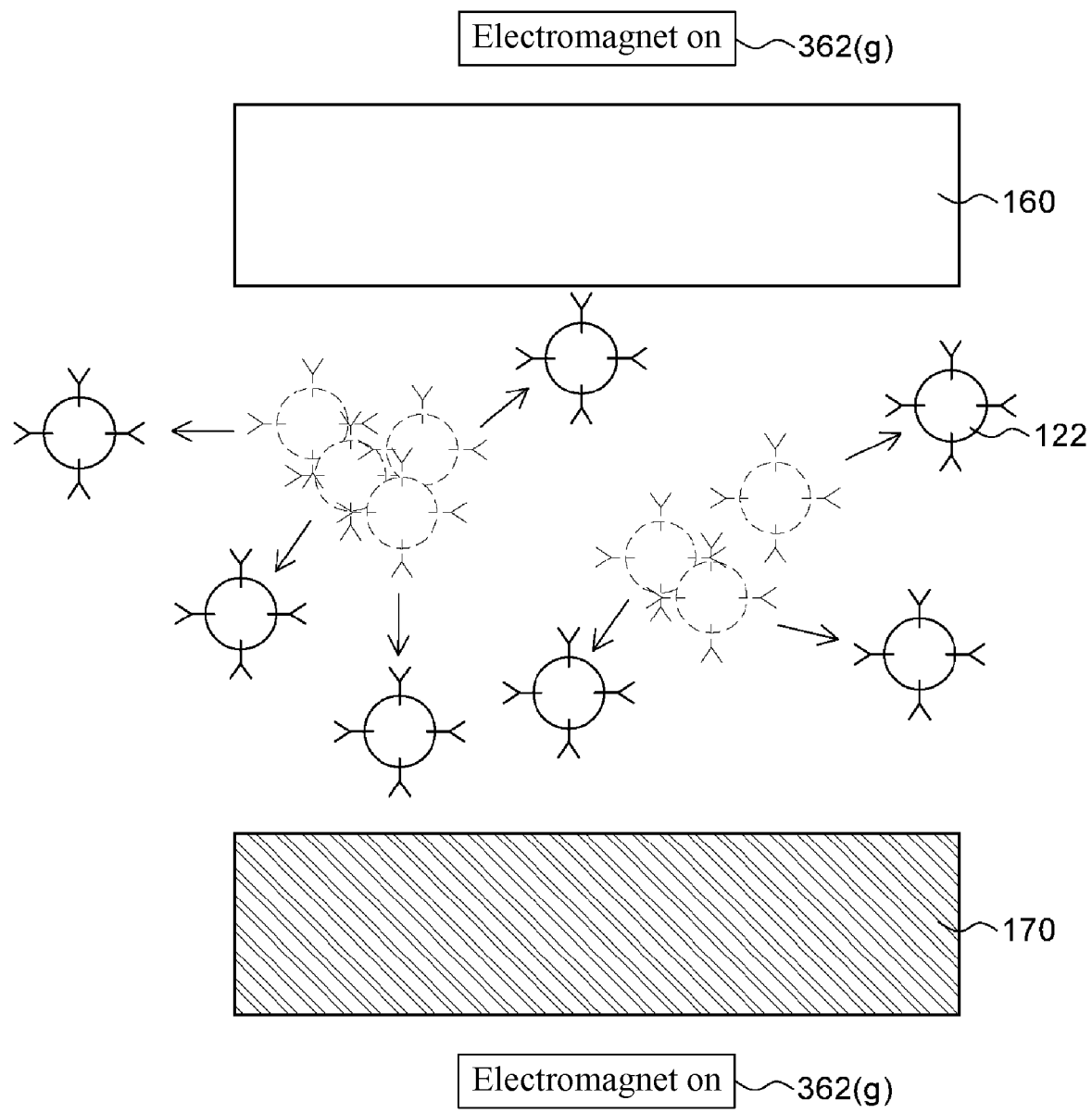
Figure 3H:
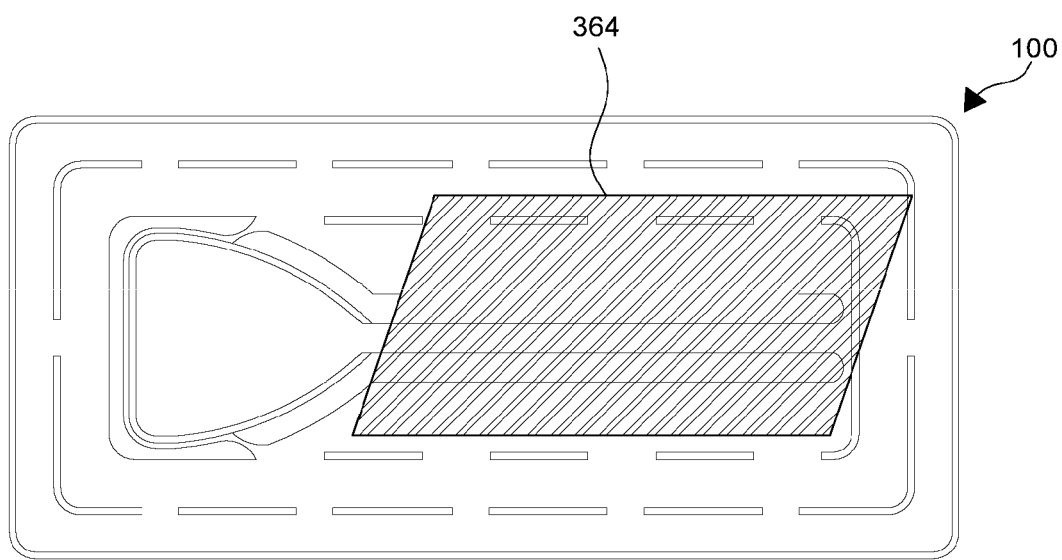
FIG. 3H is a plan view illustrating a detection channel of a microchip for analyzing fluids according to an embodiment of the present invention and a second magnetic force application part of a detector arranged therein.
Figure 3I:
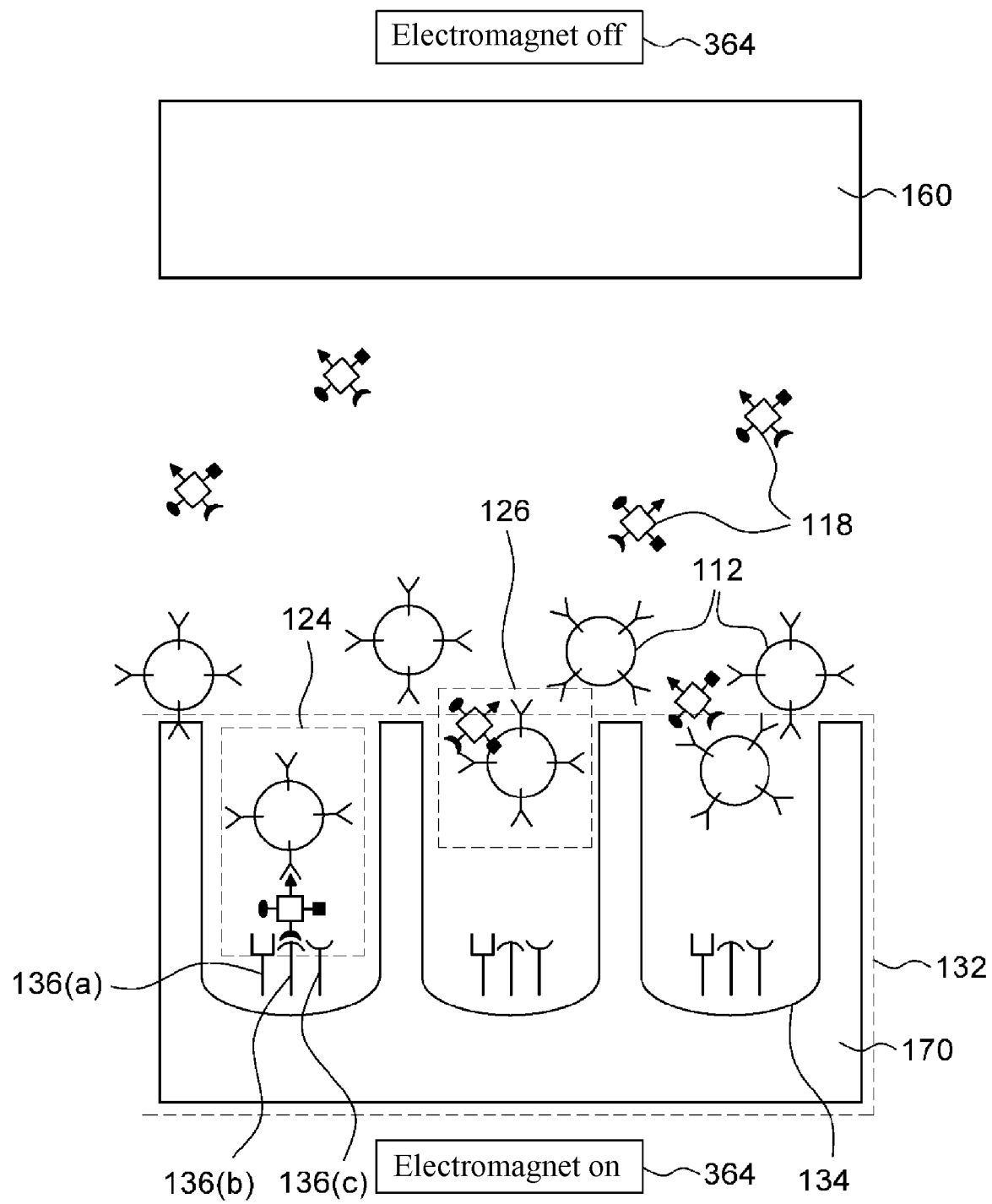
FIGS. 3I to 3K illustrate side views of a detection channel of a microchip for analyzing fluids according to an embodiment of the present invention and enlarged views of a main part for illustrating a process of detecting a detection target substance in the detection channel.
Figure 3J:
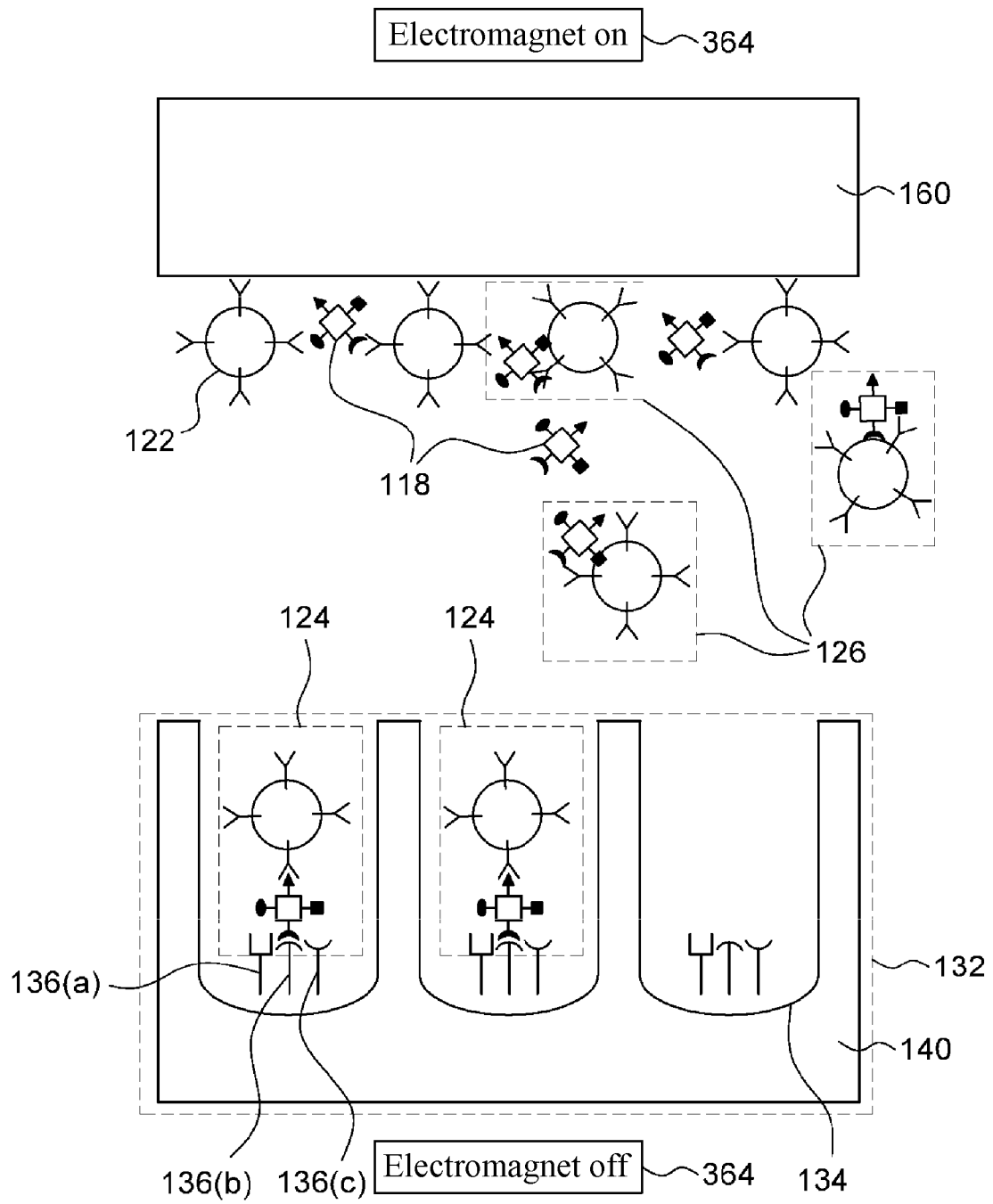
Figure 3K:
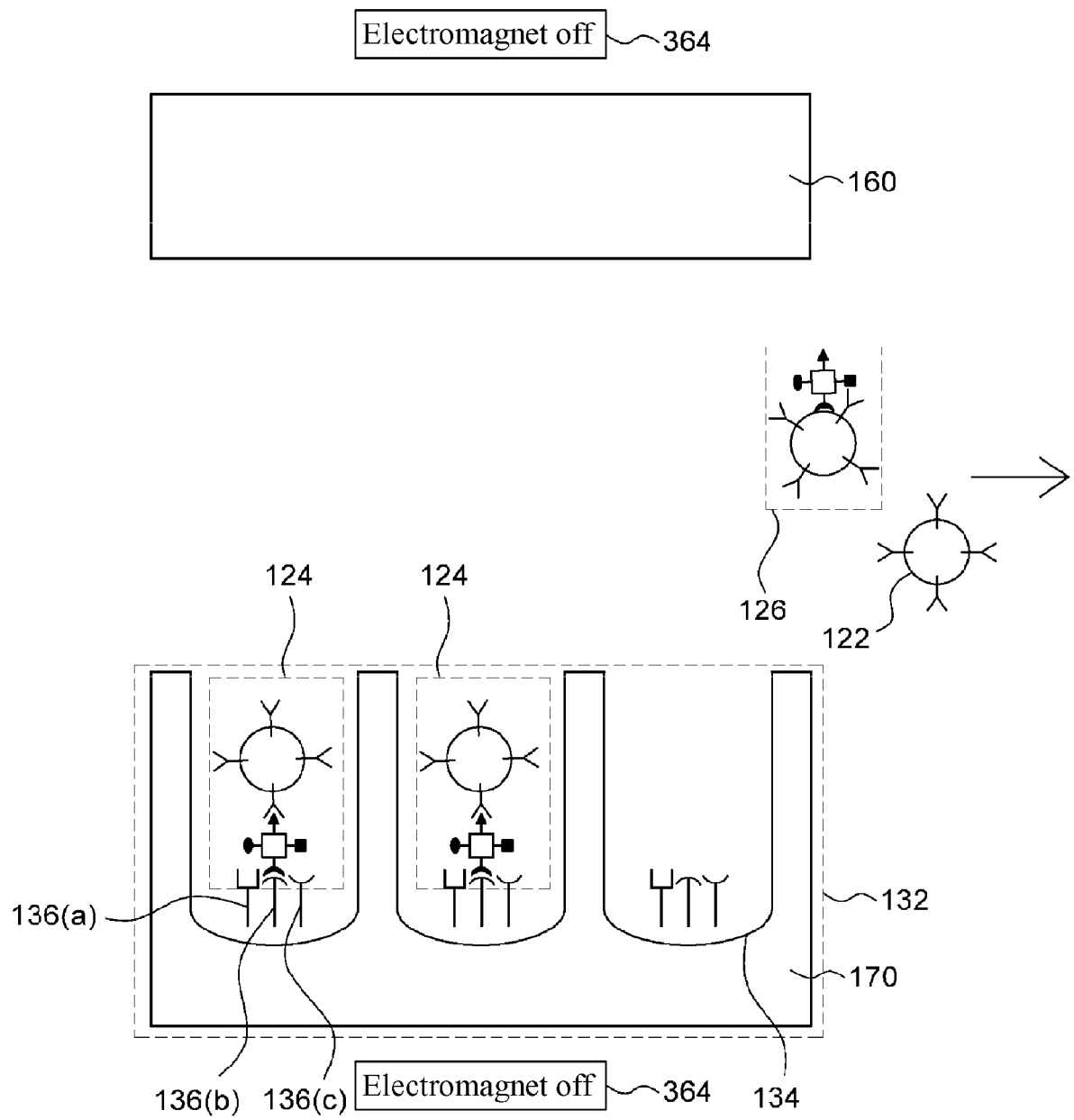

Referring to FIGS. 3F to 3G, the plurality of core magnetic materials 362 (g) disposed on the upper and lower surfaces 160 and 170 of the reaction channel 120 may be electromagnets whose electromagnetic force is adjusted according to the flow of current. Meanwhile, the magnetic particle-first antibody complexes 122 may aggregate in the reaction channel 120 (FIG. 3F). Here, electromagnetic force may be applied to all of the plurality of core magnetic materials 362 (g) positioned on the upper surface 160 and the lower surface 170 (electromagnet on), and, as a result, electromagnetic force may act perpendicular to the upper surface 160 and the lower surface 170. Accordingly, the aggregated magnetic particle-first antibody complexes 122 may be re-dispersed (FIG. 3G). As a result, the flow of the magnetic particle-first antibody complexes 122 may be controlled, and the efficiency of the first antigen-antibody reaction between the detection target antigens 118 and the magnetic particle-first antibody complexes 122 may be increased.

Referring to FIG. 3H, the second magnetic force application part 364 disposed on the detection channel 130 may be an electromagnet with a single structure configured such that electromagnetic force is applied to all surfaces of the detection channel 130. However, the shape of the second magnetic force application part 364 is not limited to the illustrated shape, and may be varied so long as electromagnetic force can be optionally applied. For example, when the second magnetic force application part 364 is a polyhedron, a magnetically controlled circular gradient may be formed to prevent the concentration of magnetic force at each corner. When such a circular gradient is formed in the second magnetic force application part 364, the magnetic particle-first antibody complexes 122 may be induced to uniformly flow in the detection channel 130.

Referring to FIG. 3I, when electromagnetic force is applied to the second magnetic force application part 364 corresponding to the lower surface 170 to which the second antibody 136 is immobilized (electromagnet on), the magnetic particle-first antibody complexes 122 including the magnetic particles 122 (b) and the immune complexes 124 may migrate toward the lower surface 170. Here, the magnetic field strength of the second magnetic force application part 364 corresponding to the lower surface 170 may be 20 to 32 mT. As a result of application of electromagnetic force to the second magnetic force application part 364 corresponding to the lower surface 170, the efficiency of the second antigen-antibody reaction between the immune complexes 124 and the second antibody 136 increases and, accordingly, the immune complexes 124 may be captured in the wells 134. Meanwhile, application of electromagnetic force to the second magnetic force application part 364 corresponding to the lower surface 170 may cause non-specific immune complexes 126, formed by a non-specific antigen-antibody reaction between the magnetic particle-first antibody complexes 122 and the detection target antigens 118, to be captured in the wells 134.

Referring to FIG. 3J, the magnetic force-applied second magnetic force application part 364 corresponding to the lower surface 170 as shown in FIG. 3I loses the electromagnetic force (electromagnet off), and magnetic force may only be applied to the second magnetic force application part 364 corresponding to the upper surface 160 (electromagnet on). Here, the magnetic field strength of the second magnetic force application part 364 corresponding to the upper surface 160 may be 32 to 39 mT. As a result of application of electromagnetic force to the second magnetic force application part 364 corresponding to the upper surface 160, the magnetic particle-first antibody complexes 122 that have not been subjected to the first antigen-antibody reaction with the detection target antigens 118 and the non-specific immune complexes 126 may migrate toward the upper surface 160. Accordingly, only the immune complexes 124 captured by the second antigen-antibody reaction with the second antibody 136 remain in the wells 134. That is, under the condition that electromagnetic force is applied to the second magnetic force application part 364 corresponding to the upper surface 160, the magnetic particle-first antibody complexes 122, the non-specific immune complexes 126, and the immune complexes 124 may be detected in the detection channel 130.

Referring to FIG. 3K, as the magnetic force-applied second magnetic force application part 364 corresponding to the upper surface 160 as shown in FIG. 3J loses the electromagnetic force (electromagnet off), all of the plurality of second magnetic force application parts 364 corresponding to the upper and lower surfaces 160 and 170 lose the magnetic force (electromagnet off). As a result, the detection target antigens 118 that have migrated toward the upper surface 160; the magnetic particle-first antibody complexes 122 that have not been subjected to the first antigen-antibody reaction; and the non-specific immune complexes 126 may escape the detection channel 130. That is, under the condition that all of the second magnetic force application parts 364 corresponding to the upper surface 160 and the lower surface 170 lose the magnetic force, the immune complexes 124 may only be detected in the detection channel 130. In addition, even if the first antibody 122 (a) and the second antibody 136 are not fluorescence-labeled antibodies, the first antibody 122 (a) and the second antibody 136 may be counted by obtaining an image at a corresponding height in the wells 134 and detecting the immune complexes 124 in the obtained image, as described above, which allows quantitative analysis of the detection target antigens 118.

Next, in the counting step (S240), the number of the immune complexes 124 may be counted as the CMOS image sensor 370 operates. In particular, a non-isotopic light source 310 passes through the pinhole aperture 320 according to light transmitted from the outside of the antigen quantitative analysis system 300. Here, the pinhole aperture 320 may include a plurality of pinholes 322. The non-isotopic light source 310 may pass through the pinholes 322, and then may be converted into the spatially isotropic light source 330. The spatially isotropic light source 330 may pass through the wavelength filter 340, and then may be converted into the isotope light source 350. That is, as a result of the step (S230) of applying electromagnetic force, the detection channel 130 including captured immune complexes 134 may be irradiated with the isotope light source 350. Here, the wells 134 may be divided into wells 134 (a) in which the immune complexes 124 are not captured; and wells 134 (b) in which the immune complexes 124 are captured. These wells 134 may be recognized by the CMOS image sensor 370. That is, the number of the wells 134 (b), in which the immune complexes 124 are captured, discriminated by the CMOS image sensor 370 may correspond to the number of the immune complexes 124. As a result, quantitative analysis of the detection target antigens 118 may be indirectly performed as the number of the immune complexes 124 is counted.

Example 1: Flow Rate Setting for Assay Sample to Maximize Accuracy of Immune Response Hereinafter, a result of evaluation for flow rate setting of an assay sample to maximize the accuracy of an immune response, using the microchip for analyzing fluids according to an embodiment of the present invention and the method of quantitating an antigen according to another embodiment of the present invention, is described with reference to FIG. 4.

Figure 4:
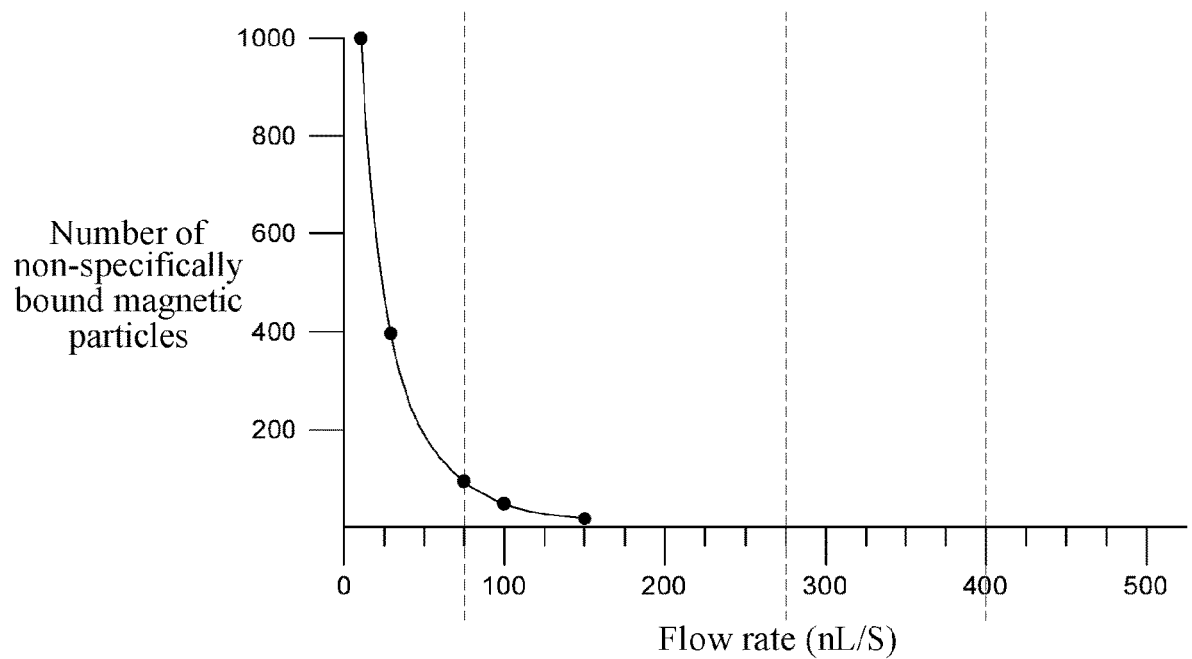
FIG. 4 illustrates an experimental result for determining a flow rate of an assay sample to maximize the accuracy of an immune response, using a microchip for analyzing fluids according to an embodiment of the present invention and a method of quantitating an antigen according to another embodiment of the present invention.

FIG. 4 illustrates an experimental result for determining a flow rate of an assay sample to maximize the accuracy of an immune response, using the microchip for analyzing fluids according to an embodiment of the present invention and the method of quantitating an antigen according to another embodiment of the present invention. Referring to FIG. 4, in the case of a fluid-type assay sample having a flow rate of 75 nL/s or less, a plurality of non-specifically bound magnetic particles is detected in the detection channel of the microchip for analyzing fluids according to an embodiment of the present invention. Meanwhile, as a flow rate of an assay sample increases to 75 nL/s or more, the number of non-specifically bound magnetic particles appears to decrease. Further, when a flow rate is 280 nL/s or more, an assay sample may have a drag that can break antigen-antibody binding of an immune complex. Accordingly, few non-specifically bound magnetic particles appear to be captured in the detection channel of the microchip for analyzing fluids at a flow rate of 280 nL/s or more.

In addition, when an assay sample has a flow rate of 280 nL/s to 400 nL/s, immune complexes captured in the plurality of wells or capture pillars in the detection channel of the microchip for analyzing fluids according to an embodiment of the present invention are less subject to drag according to the flow of the assay sample, so that the immune complexes may be immobilized between the wells or capture pillars. Meanwhile, non-specifically bound magnetic particles or nonspecific immune complexes may be removed according to the flow of the assay sample.

As a result of Example 1, components of the microchip for analyzing fluids according to an embodiment of the present invention may be disposed to have a flow rate of 100 nL/s to 500 nL/s, preferably a flow rate of 200 nL/s to 400 nL/s, due to different immune response between assay samples. For example, the channels of the microchip for analyzing fluids according to an embodiment of the present invention may be provided with flow control pillars such that an assay sample has a flow rate of 280 nL/s to 400 nL/s. Further, the lower surface constituting the body of the microchip for analyzing fluids according to an embodiment of the present invention may be formed at different heights for each channel such that an assay sample has a flow rate of 280 nL/s to 400 nL/s.

Example 2: Evaluation of Microchip for Analyzing Fluids According to Embodiment of Present Invention and Method of Quantitating Antigen According to Another Embodiment of Present Invention Hereinafter, evaluation results of the microchip for analyzing fluids according to an embodiment of the present invention and the method of quantitating an antigen according to another embodiment of the present invention are described with reference to FIGS. 5A and 5B. In this evaluation, a nuclear protein of influenza A virus was set as a detection target antigen, and five repetitive experiments were performed at five concentrations. In particular, the five concentrations of the nuclear protein of influenza A virus used for the evaluation were 0 pM, 0.1 pM, 1 pM, 10 pM and 100 pM.

Figure 5A:
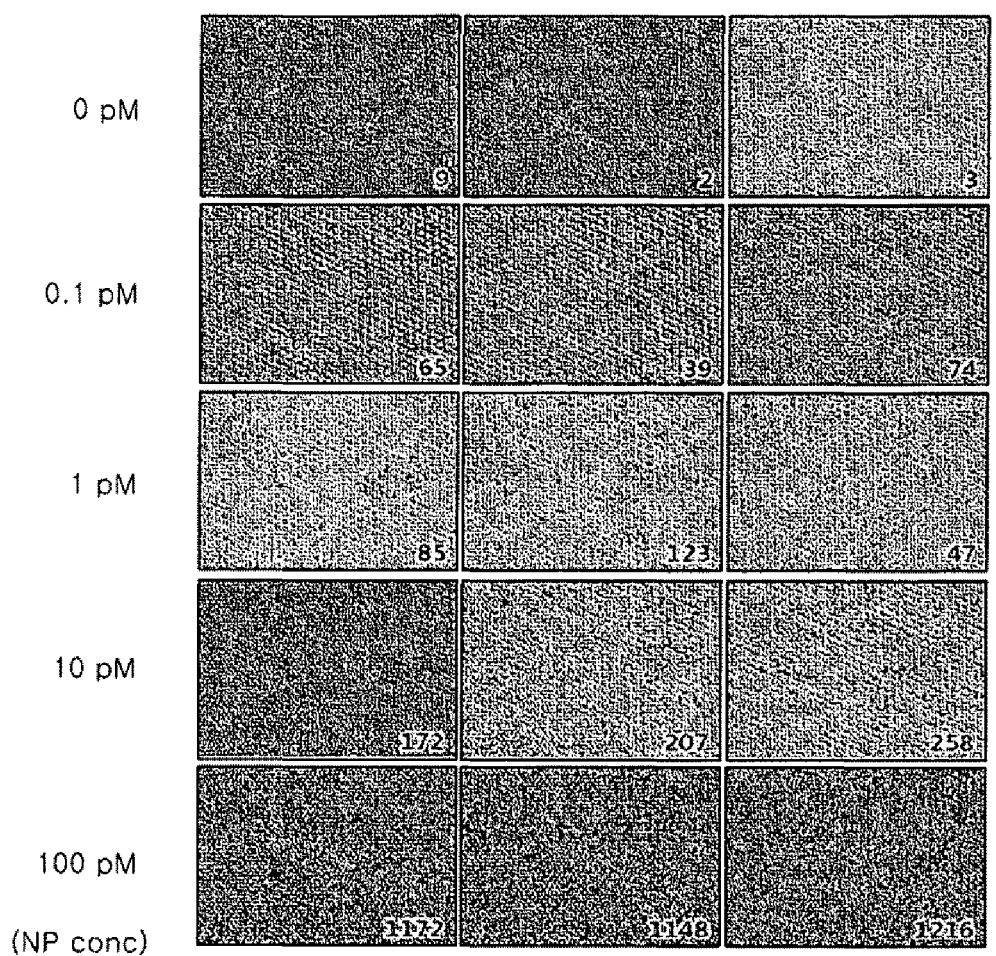
FIGS. 5A and 5B illustrate evaluation results of a microchip for analyzing fluids according to an embodiment of the present invention and a method of quantitating an antigen according to another embodiment of the present invention.
Figure 5B:
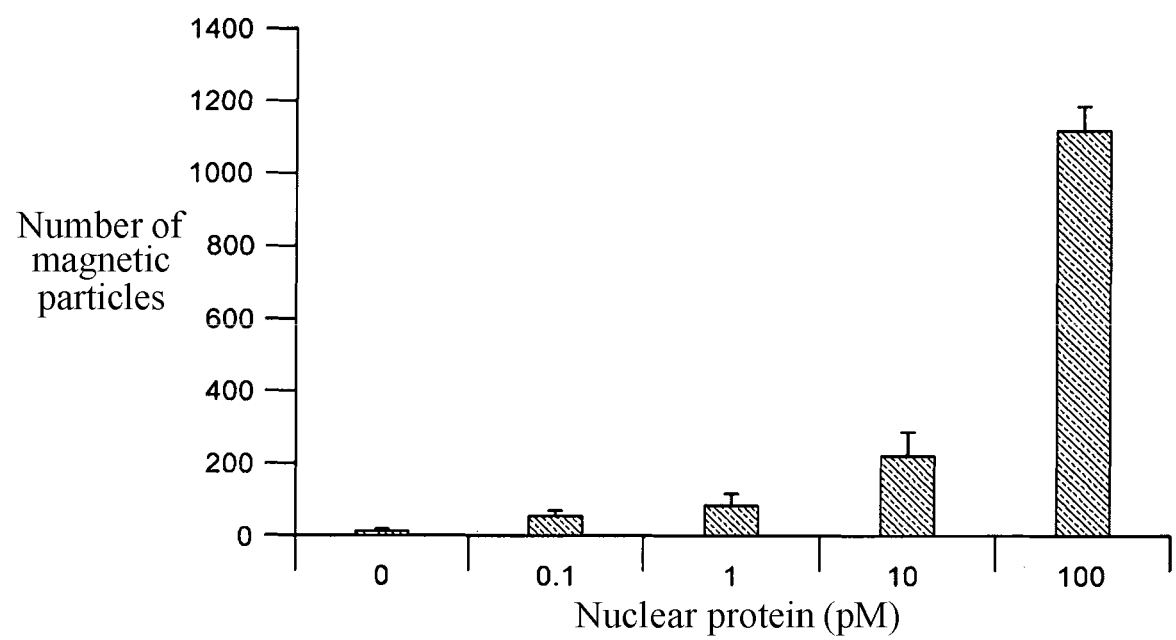

FIGS. 5A and 5B illustrate evaluation results of the microchip for analyzing fluids according to an embodiment of the present invention and the method of quantitating an antigen according to another embodiment of the present invention.

FIG. 5A illustrates images of a portion of the detection channel 130 of the microchip 100 for analyzing fluids according to an embodiment of the present invention.

In a detection channel to which the nuclear protein of influenza A virus was not added, 9, 2, 3, 2 and 15 magnetic particles were observed for each repeated experiment. Such particle numbers may represent the number of magnetic particles that did not exit the detection channel according to the magnetic control of the electromagnet.

In a detection channel to which the nuclear protein of influenza A virus was added at a concentration of 0.1 pM, 65, 39, 74, 62 and 63 magnetic particles were observed for each repeated experiment. In addition, 85, 123, 47, 78 and 98 magnetic particles were observed for each repeated experiment in a detection channel to which the nuclear protein of influenza A virus was added at a concentration of 1 pM, and 172, 207, 258, 206 and 187 magnetic particles were observed for each repeated experiment in a detection channel to which the nuclear protein of influenza A virus was added at a concentration of 10 pM. Finally, 1172, 1148, 1216, 1064 and 1087 magnetic particles were observed for each repeated experiment in a detection channel to which the nuclear protein of influenza A virus was added at a concentration of 100 pM. Here, most of the magnetic particles constituting the immune complexes observed in the detection channels to which the nuclear protein of influenza A virus was added at the concentrations of 0.1 pM, 1 pM, 10 pM and 100 pM was confirmed as being captured in the wells.

FIG. 5B is a graph illustrating the number of magnetic particles dependent upon concentration increase of the added influenza A virus nuclear protein. As a result, it was confirmed that the number of detected magnetic particles increases proportional to an increase in the concentration of the nuclear protein of influenza A virus.

As shown in Example 2, the microchip for analyzing fluids according to an embodiment of the present invention and the method of quantitating an antigen according to another embodiment of the present invention allow detection of a detection target antigen, present in a trace amount of a pM unit in an assay sample, with high sensitivity. For example, when the microchip for analyzing fluids according to an embodiment of the present invention is introduced into a detector including a magnetic material, nonspecific immune complexes or magnetic particles that do not react with a detection target antigen are washed away, which allows highly accurate detection of the detection target antigen.

In particular, capillary force and electromagnetic force, which are main driving forces for a fluid sample, may allow the microchip for analyzing fluids according to an embodiment of the present invention to exhibit a uniform fluid movement pattern. As a result, the microchip for analyzing fluids according to an embodiment of the present invention may overcome obstacles in detection and analysis due to non-uniform fluid movement patterns of conventional microchips for analyzing fluids.

Further, the microchip for analyzing fluids according to an embodiment of the present invention and the method of quantitating an antigen according to another embodiment of the present invention may count the number of magnetic particles without using a fluorescence-labeled antibody, thus allowing indirect quantitative analysis of a detection target antigen.

Although the embodiments of the present invention have been described in more detail with reference to the accompanying drawings, the present invention is not limited to the embodiments, and may be modified into various forms without departing from the technical spirit of the present invention. Thus, the embodiments disclosed in the present invention are not intended to limit the technical idea of the present invention but to describe the present invention, and the scope of the technical idea of the present invention is not limited by the embodiments. Therefore, it should be understood that the embodiments described above are exemplary in all respects and not restrictive. The protection scope of the present invention should be interpreted by the following claims, and all technical ideas within the equivalent scope should be interpreted as being included in the scope of the present invention.

The invention claimed is:
1. An analysis device comprising:
   a microchip;
   a first upper magnetic force application part disposed above the microchip and a first lower magnetic force application part disposed below the microchip;
   a second upper magnetic force application part disposed above the microchip and a second lower magnetic force application part disposed below the microchip; and
   a sensor,
   wherein the microchip comprises:
   a body including an upper portion and a lower portion; and
   a plurality of internal channels formed between the upper portion and the lower portion,
   wherein the plurality of internal channels comprise:
      an input channel having an input channel upper surface and an input channel lower surface and configured to receive an assay sample including target antigens and injected through a through hole penetrating the upper portion of the body,
      a reaction channel having a reaction channel upper surface and a reaction channel lower surface and configured to be in fluid communication with the input channel and including magnetic particle-first antibody complexes to be subjected to a first antigen-antibody reaction with the target antigens in the assay sample flowed from the input channel, wherein the magnetic particle-first antibody complexes include magnetic particles and first antibodies, and the magnetic particle-first antibody complexes and the target antigens form immune complexes through the first antigen-antibody reaction, and a detection channel having a detection channel upper surface and a detection channel lower surface and configured to be in fluid communication with the reaction channel and including second antibodies to be subjected to a second antigen-antibody reaction with the immune complexes flowed from the reaction channel, wherein the input channel upper surface of the input channel, the reaction channel upper surface of the reaction channel and the detection channel upper surface of the detection channel constitute the upper portion of the body, wherein the input channel lower surface of the input channel, the reaction channel lower surface of the reaction channel and the detection channel lower surface of the detection channel constitute the lower portion of the body, wherein the reaction channel lower surface of the reaction channel has a higher height than the input channel lower surface of the input channel, wherein the detection channel has a longer length than each of a length of the input channel and a length of the reaction channel, wherein the detection channel has a narrower width than each of a width of the input channel and a width of the reaction channel, wherein the microchip further comprises flow control pillars for controlling flow of the assay sample, and wherein the flow control pillars comprise a control pillar attached to the reaction channel upper surface of the reaction channel for physically regulating flow of the magnetic particle-first antibody complexes and a control pillar attached to the detection channel upper surface of the detection channel, wherein the sensor is configured to count the number of the target antigens in the assay sample, wherein each of the first upper magnetic force application part and the first lower magnetic force application part is disposed at a position corresponding to the reaction channel, wherein each of the first upper magnetic force application part and the first lower magnetic force application part comprises a core magnetic material and a plurality of magnetic material pairs protruding from the core magnetic material and surrounding the core magnetic material, wherein the plurality of magnetic material pairs include:
a first magnetic material pair protruding from the core magnetic material,
a second magnetic material pair protruding from the core magnetic material and adjacent to the first magnetic material pair, and
a third magnetic material pair protruding from the core magnetic material and adjacent to the second magnetic material pair, and wherein the device is configured to sequentially apply electromagnetic force to the first magnetic material pair, the second magnetic material pair and the third magnetic material pair so that the magnetic particle-first antibody complexes rotate in the reaction channel, wherein each of the second upper magnetic force application part and the second lower magnetic force application part is disposed at a position corresponding to the detection channel, and wherein the device is further configured to control application of electromagnetic force to the second upper magnetic force application part and the second lower magnetic force application part to control flow of the magnetic particle-first antibody complexes.

2. The device according to claim 1, wherein a height of the reaction channel lower surface of the reaction channel decreases from a start portion of the reaction channel toward the detection channel.

3. The device according to claim 1, wherein the magnetic particles have a particle diameter of 0.1 to 6.0 μm.

4. The device according to claim 1, wherein the first antibodies and the second antibodies are not fluorescence-labeled antibodies.

5. The device according to claim 1, wherein the first antibodies are monoclonal antibodies, and the second antibodies are polyclonal antibodies.

6. The device according to claim 1, wherein the input channel comprises a filter.

7. The device according to claim 1, wherein the assay sample has a flow rate of 100 to 500 nL/s.

8. The device according to claim 1, wherein the device is further configured to adjust electromagnetic force of the core magnetic material of each of the first upper magnetic force application part and the first lower magnetic application part to aggregate or disperse the magnetic particle-first antibody complexes in the reaction channel.

9. The device according to claim 1, wherein the detection channel comprises a plurality of wells, and the second antibodies are immobilized in the wells via a linker molecule.

10. The device according to claim 9, wherein a diameter and depth of each of the plurality of wells are 1.2 to 2.0 times a particle diameter of the magnetic particle- first antibody complexes.

11. The device according to claim 1, wherein the detection channel further comprises a plurality of capture pillars, and the second antibodies are immobilized between the capture pillars.

12. The device according to claim 11, wherein the plurality of capture pillars are spaced by a length of 1.2 to 2.0 times a particle diameter of the magnetic particle-first antibody complexes.

13. A method of quantitating an antigen, the method comprising:
positioning the assay sample in the input channel of the microchip of the device of claim 1;
introducing the microchip into a detector comprising a first upper magnetic force application part, a first lower magnetic force application part, a second upper magnetic force application part, and a second lower magnetic force application part, and a CMOS image sensor;
applying electromagnetic force to the first upper magnetic force application part and the first lower magnetic force application part;
controlling application of electromagnetic force to the second upper magnetic force application part and the second lower magnetic force application part; and
counting the number of the target antigens in the assay sample using the CMOS image sensor,
wherein each of the first upper magnetic force application part and the first lower magnetic force application part is disposed at a position corresponding to the reaction channel,
wherein each of the first upper magnetic force application part and the first lower magnetic force application part comprises a core magnetic material and a plurality of magnetic material pairs protruding from the core magnetic material and surrounding the core magnetic material,
wherein the plurality of magnetic material pairs include:
a first magnetic material pair protruding from the core magnetic material,
a second magnetic material pair protruding from the core magnetic material and adjacent to the first magnetic material pair, and
a third magnetic material pair protruding from the core magnetic material and adjacent to the second magnetic material pair, and
wherein the applying of the electromagnetic force to the first upper magnetic force application part and the first lower magnetic force application part comprises sequentially applying electromagnetic force to the first magnetic material pair, the second magnetic material pair and the third magnetic material pair so that the magnetic particle-first antibody complexes rotate in the reaction channel,
wherein each of the second upper magnetic force application part and the second lower magnetic force application part is disposed at a position corresponding to the detection channel,
wherein the controlling of application of the electromagnetic force to the second upper magnetic force application part and the second lower magnetic force application part comprises controlling the application of the electromagnetic force to the second upper magnetic force application part and the second lower magnetic force application part to control flow of the magnetic particle-first antibody complexes in the detection channel.

14. The method according to claim 13, wherein the applying of electromagnetic force to the first upper magnetic force application part and the first lower magnetic force application part comprises adjusting electromagnetic force of the core magnetic material of each of the first upper magnetic force application part and the first lower magnetic application part to aggregate or disperse the magnetic particle-first antibody complexes in the reaction channel.

15. The method according to claim 13, wherein the controlling of the application of electromagnetic force to the second upper and lower magnetic force application parts comprises applying electromagnetic force only to the second lower magnetic force application part disposed to correspond to the detection channel lower surface of the detection channel such that the immune complexes are captured on the detection channel lower surface; and applying electromagnetic force only to the second upper magnetic force application part corresponding to the detection channel upper surface of the detection channel such that the magnetic particles floating in the detection channel migrate to the detection channel upper surface.

16. The method according to claim 15, wherein the controlling of the application of electromagnetic force to the second upper and lower magnetic force application parts further comprises completely blocking electromagnetic force of the second upper and lower magnetic force application parts such that the floating magnetic particles exit the detection channel, after applying electromagnetic force only to the second upper magnetic force application part corresponding to the detection channel upper surface.

* * * * *